(12) United States Patent
Blanco-Pillado et al.

(10) Patent No.: US 10,005,721 B2
(45) Date of Patent: Jun. 26, 2018

(54) DIMETHYLBENZOIC ACID COMPOUNDS

(71) Applicant: Eli Lilly and Company, Indianapolis, IN (US)

(72) Inventors: Maria Jesus Blanco-Pillado, Fishers, IN (US); Peter Rudolph Manninen, Brownsburg, IN (US); Matthew Allen Schiffler, Indianapolis, IN (US); Tatiana Natali Vetman, Greenwood, IN (US); Alan M Warshawsky, Carmel, IN (US); Jeremy Schulenburg York, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days. days.

(21) Appl. No.: 15/030,891

(22) PCT Filed: Dec. 11, 2014

(86) PCT No.: PCT/US2014/069783
§ 371 (c)(1),
(2) Date: Apr. 21, 2016

(87) PCT Pub. No.: WO2015/094912
PCT Pub. Date: Jun. 25, 2015

(65) Prior Publication Data
US 2016/0251306 A1    Sep. 1, 2016

Related U.S. Application Data

(60) Provisional application No. 61/916,824, filed on Dec. 17, 2013.

(51) Int. Cl.
| | |
|---|---|
| *C07C 235/84* | (2006.01) |
| *C07D 213/81* | (2006.01) |
| *C07D 215/52* | (2006.01) |
| *C07D 401/12* | (2006.01) |
| *C07C 233/81* | (2006.01) |
| *C07C 235/42* | (2006.01) |
| *C07D 405/04* | (2006.01) |

(52) U.S. Cl.
CPC .......... *C07C 235/84* (2013.01); *C07C 233/81* (2013.01); *C07C 235/42* (2013.01); *C07D 213/81* (2013.01); *C07D 215/52* (2013.01); *C07D 401/12* (2013.01); *C07D 405/04* (2013.01)

(58) Field of Classification Search
USPC ................................ 514/318, 354, 522, 563
See application file for complete search history.

(56) References Cited

U.S. PATENT DOCUMENTS

| | | | |
|---|---|---|---|
| 7,705,035 B2 | 4/2010 | Boyd et al. | |
| 8,642,768 B2 | 2/2014 | Blanco-Pillado et al. | |
| 8,933,098 B2 | 1/2015 | Blanco-Pillado et al. | |
| 2005/0256170 A1 | 11/2005 | Oxford | |
| 2011/0288100 A1 | 11/2011 | Sun | |
| 2012/0083463 A1 | 4/2012 | Maue et al. | |
| 2014/0005222 A1* | 1/2014 | Blanco-Pillado .... | C07D 401/04 514/313 |

FOREIGN PATENT DOCUMENTS

| | | |
|---|---|---|
| EP | 2765128 | 8/2014 |
| WO | WO9602509 | 2/1996 |
| WO | WO2012117097 | 9/2012 |
| WO | WO2014/122267 A1 * | 8/2014 ........... C07C 255/57 |

* cited by examiner

*Primary Examiner* — Pancham Bakshi
(74) *Attorney, Agent, or Firm* — Nelsen L. Lentz

(57) ABSTRACT

The present invention provides a compound of the Formula I: wherein A is: and W, Y, X, $R^1$, $R^2$, $R^3$, and $R^4$ are as defined herein, or a pharmaceutically acceptable salt thereof, for use as an inhibitor of the EP4 receptor.

7 Claims, No Drawings

DIMETHYLBENZOIC ACID COMPOUNDS

The present invention relates to certain novel dimethylbenzoic acid compounds, to pharmaceutical compositions comprising the compounds, to methods of using the compounds to treat physiological disorders, and to intermediates and processes useful in the synthesis of the compounds.

The present invention is in the field of treatment of inflammatory conditions, such as arthritis, including osteoarthritis and rheumatoid arthritis, and further including pain associated with these conditions. Arthritis affects millions of patients in the United States alone and is a leading cause of disability. Treatments often include NSAIDs (non-steroidal anti-inflammatory drugs) or COX-2 inhibitors, which may produce untoward cardiovascular side effects. As such, patients who have a poor cardiovascular profile, such as hypertension, may be precluded from using NSAIDs or COX-2 inhibitors. Thus, there is a need for an alternative treatment of osteoarthritis and rheumatoid arthritis, preferably without the side effects of the current treatments.

Four prostaglandin $E_2$ ($PGE_2$) receptor subtypes have been identified as the following: EP1, EP2, EP3 and EP4. It has been disclosed that EP4 is the primary receptor involved in joint inflammatory pain in rodent models of rheumatoid arthritis and osteoarthritis. Hence, a selective EP4 antagonist may be useful in treating arthritis, including arthritic pain. In addition, it has been suggested that since EP4 antagonism does not interfere with biosynthesis of prostanoids, such as $PGI_2$ and $TxA_2$, a selective EP4 antagonist may not possess the potential cardiovascular side effects seen with NSAIDs and COX-2 inhibitors.

WO 96/02509 discloses certain quinoline derivatives which are selective, non-peptide $NK_3$ antagonists useful in treating a variety of disorders including, for example, pulmonary disorders, CNS disorders, neurogenic inflammation, and inflammatory pain. In addition, U.S. Pat. No. 7,705,035 discloses certain indoline amide derivatives useful as EP4 ligands, agonists, or antagonists useful in treating various disorders, such as osteoarthritis, rheumatoid arthritis, and acute and chronic pain.

The present invention provides certain novel compounds that are inhibitors of EP4 and certain novel compounds that are selective inhibitors of EP4 relative to EP1, EP2, and EP3. In addition, the present invention provides certain novel compounds with the potential for reduced cardiovascular or gastrointestinal side effects in comparison to traditional NSAIDs.

Accordingly, the present invention provides a compound of the Formula I:

Formula I wherein A is:

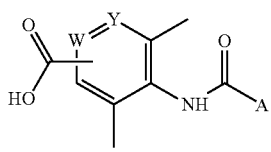

or

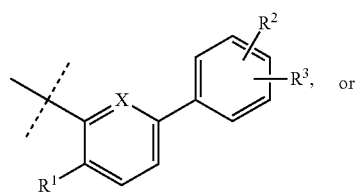

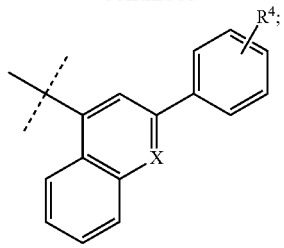

W is CH or N;
Y is CH or N;
X is CH or N;
$R^1$ is $CH_3$, $CF_3$, or F;
$R^2$ is H, F, Cl, $CH_3$, $CF_3$, $CH_2OH$, $CH_2CH_2OH$, $CH_2OCH_3$, $OCH_3$, $OCF_3$, or CN;
$R^3$ is H or F; or
$R^2$ and $R^3$ together are a $OCH_2O$ group attached to vicinal carbon atoms;
$R^4$ is H, Cl, or $CH_2OH$;
or a pharmaceutically acceptable salt thereof.

The present invention also provides a method of treating arthritis in a patient, comprising administering to a patient in need of such treatment an effective amount of a compound of Formula I, or a pharmaceutically acceptable salt thereof. The present invention also provides a method of treating osteoarthritis in a patient, comprising administering to a patient in need of such treatment an effective amount of a compound of Formula I, or a pharmaceutically acceptable salt thereof. In addition, the present invention provides a method of treating rheumatoid arthritis in a patient, comprising administering to a patient in need of such treatment an effective amount of a compound of Formula I, or a pharmaceutically acceptable salt thereof. The present invention also provides a method of treating pain associated with arthritis in a patient, comprising administering to a patient in need of such treatment an effective amount of a compound of Formula I, or a pharmaceutically acceptable salt thereof. The present invention further provides a method of treating pain associated with osteoarthritis or rheumatoid arthritis in a patient, comprising administering to a patient in need of such treatment an effective amount of a compound of Formula I, or a pharmaceutically acceptable salt thereof.

Furthermore, the invention provides a compound of Formula I, or a pharmaceutically acceptable salt thereof for use in therapy. In addition, the invention provides a compound of Formula I, or a pharmaceutically acceptable salt thereof for use in the treatment arthritis. In particular, the invention provides a compound of Formula I, or a pharmaceutically acceptable salt thereof for use in the treatment of osteoarthritis. In addition, the invention provides a compound of Formula I, or a pharmaceutically acceptable salt thereof for use in the treatment of rheumatoid arthritis. The invention also provides a compound of Formula I, or a pharmaceutically acceptable salt thereof for use in the treatment of pain associated with arthritis. The invention also provides a compound of Formula I, or a pharmaceutically acceptable salt thereof for use in the treatment of pain associated with osteoarthritis or rheumatoid arthritis. Furthermore, the invention provides the use of a compound of Formula I, or a pharmaceutically acceptable salt thereof, for the manufacture of a medicament for the treatment of arthritis. In addition, the invention provides the use of a compound of Formula I, or a pharmaceutically acceptable salt thereof, for the manufacture of a medicament for the treatment of osteoarthritis. The invention provides the use of a compound of Formula I, or a pharmaceutically acceptable salt thereof, for the manufacture of a medicament for the treatment of rheumatoid arthritis. The present invention also provides the use of a compound of Formula I, or a pharmaceutically acceptable salt thereof, for the manufacture of a medicament for the treatment of pain associated with osteoarthritis or rheumatoid arthritis.

The invention further provides a pharmaceutical composition comprising a compound of Formula I, or a pharmaceutically acceptable salt thereof, with one or more pharmaceutically acceptable carriers, diluents, or excipients. This invention also encompasses novel intermediates and processes for the synthesis of the compound of Formula I, or a pharmaceutically acceptable salt thereof.

As used herein, the terms "treating" or "to treat" includes restraining, slowing, stopping, or reversing the progression or severity of an existing symptom or disorder.

As used herein, the term "patient" refers to a mammal, such as a mouse, guinea pig, rat, cat, dog, or human. It is understood that the preferred patient is a human.

As used herein, the term "effective amount" refers to the amount or dose of the compound of the invention, or a pharmaceutically acceptable salt thereof which, upon single or multiple dose administration to the patient, provides the desired effect in the patient under diagnosis or treatment.

As used herein, the phrase "$R^2$ and $R^3$ together are a $OCH_2O$ group attached to vicinal carbon atoms" refers to the following structures, for example, wherein the corresponding oxygen atoms are attached to the vicinal carbons on the phenyl:

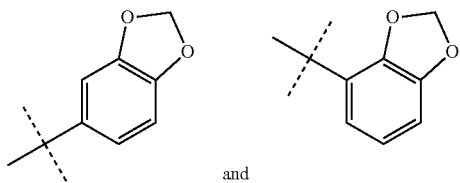

and

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I, or pharmaceutically acceptable salt thereof, are generally effective over a wide dosage range. For example, dosages per day normally fall within the range of about 0.01 to about 50 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formula I are particularly useful in the treatment methods of the invention, but certain groups, substituents, and configurations are preferred. The following paragraphs describe such preferred groups, substituents, and configurations. It will be understood that these preferences are applicable to the new compounds of the invention, and the treatment methods, uses, and pharmaceutical compositions of the invention.

Compounds of Formula Ia and Formula Ib are preferred:

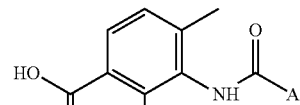

Formula Ia or

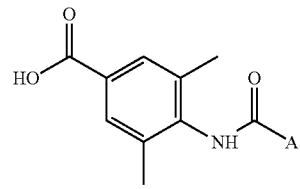

Formula Ib

Formula Ia is most preferred.

It is understood by one of ordinary skill in the art, that when the carboxylic acid is in the meta position to each of the two methyl groups on the phenyl ring as in Formula Ib above, then W must be C and not CH.

It is also preferred that A is:

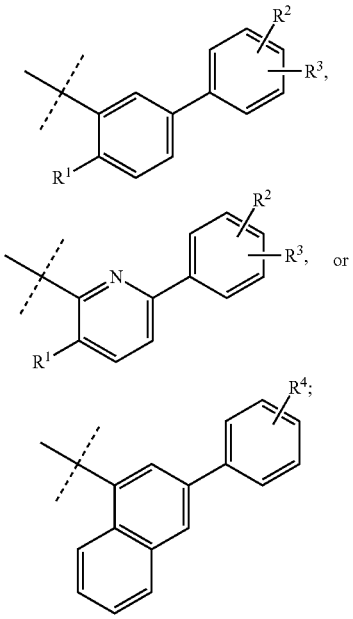

It is further preferred that A is:

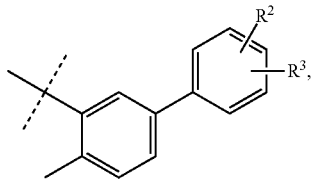

-continued

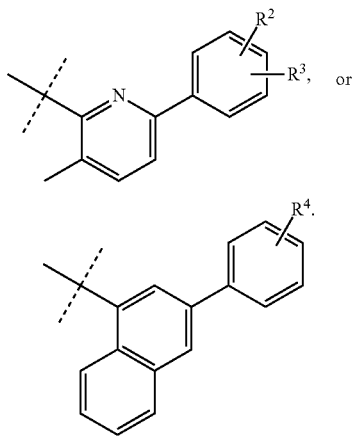

It is especially preferred that A is:

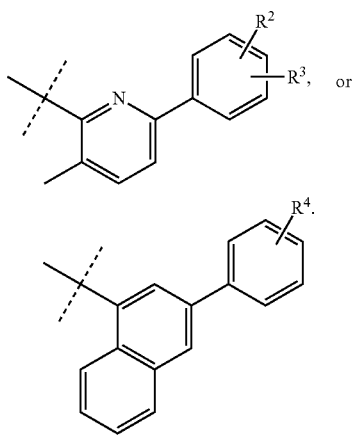

It is further especially preferred that A is:

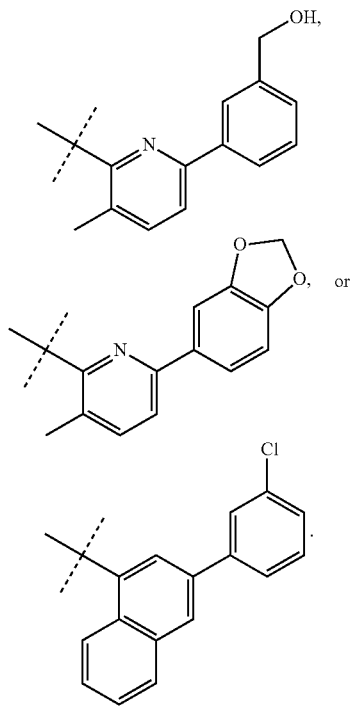

It is most especially preferred that A is:

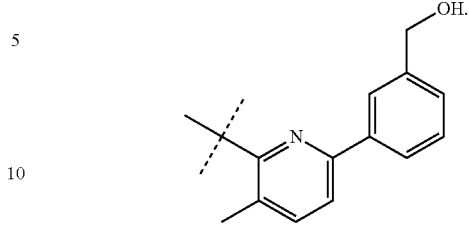

It is preferred that W is CH.
It is preferred that Y is CH.
It is most preferred that when W is CH, Y is CH.
It is preferred that $R^1$ is $CH_3$.
It is preferred that $R^2$ is $CH_2OH$, $CH_2CH_2OH$, or $OCH_3$.
It is further preferred that $R^2$ is $CH_2OH$.
It is also preferred that $R^2$ and $R^3$ together are a $OCH_2O$ group attached to vicinal carbon atoms.
It is further preferred that $R^3$ is H.
It is preferred that when $R^2$ is $CH_2OH$, $CH_2CH_2OH$, or $OCH_3$, $R^3$ is H.
It is further preferred that when $R^2$ is $CH_2OH$, $R^3$ is H.
It is preferred that $R^4$ is Cl.
Preferred compounds are:
3-[[6-(1,3-benzodioxol-5-yl)-3-methyl-pyridine-2-carbonyl]amino]-2,4-dimethyl-benzoic acid;
3-[[6-[3-(hydroxymethyl)phenyl]-3-methyl-pyridine-2-carbonyl]amino]-2,4-dimethyl-benzoic acid; and
3-[[3-(3-chlorophenyl)naphthalene-1-carbonyl]amino]-2,4-dimethyl-benzoic acid;
and the pharmaceutically acceptable salts thereof.

As used herein, "kPag" refers to kilopascals gauge pressure; "Boc" refers to a tert-butoxycarbonyl protecting group; "DMEM" refers to Dulbecco's Modified Eagle's Medium; "ACN" refers to acetonitrile; "TFA" refers to trifluoro acetic acid; "DIEA" refers to N,N-diisopropylethylamine; "DMAP" refers to 4-(N,N-dimethylamino)pyridine; "DMSO" refers to dimethylsulfoxide; "DMF" refers to N,N-dimethylformamide; "EtOH" refers to ethanol; "THF" refers to tetrahydrofuran; "MeOH" refers to methanol; "EtOAc" refers to ethyl acetate; "$Et_2O$" refers to diethyl ether; "TBME" refers to tert-butyl methyl ether; "BOP-Cl" refers to bis(2-oxo-3-oxazolidinyl)phosphonic chloride; "mCPBA" refers to 3-chloroperbenzoic acid; "KHMDS" refers to potassium bis(trimethylsilyl)amide; "h" refers to hour or hours; "$PGE_2$" refers to prostaglandin $E_2$; "FBS" refers to Fetal Bovine Serum; "IBMX" refers to (3-isobutyl-1-methylxanthine); "MES" refers to (2-(N-morpholino)ethanesulfonic acid; "HEPES" refers to (2-[4-(2-hydroxyethyl)piperazin-1-yl]ethanesulfonic acid); "S-Phos" refers to 2-dicyclohexylphosphino-2',6'-dimethoxybiphenyl; "HTRF" refers to homogeneous time-resolved fluorescence technology; "HEK" refers to human embryonic kidney; "HBSS" refers to Hank's Balanced Salt Solution; "RT" refers to room temperature; "$EC_{80}$" refers to the concentration of an agent that produces 80% of the maximal efficacy possible for that agent; and "$IC_{50}$" refers to the concentration of an agent that produces 50% of the maximal inhibitory response possible for that agent.

Pharmaceutically acceptable salts and common methodology for preparing them are well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One skilled in the art of synthesis will appreciate that the compounds of the invention are readily converted to and may be isolated as a pharmaceutically acceptable salt, such as a hydrochloride salt, using techniques and conditions well known to one of ordinary skill in the art. In addition, one skilled in the art of synthesis will appreciate that the compounds of Formula I are readily converted to and may be isolated as the corresponding free base or free acid from the corresponding pharmaceutically acceptable salt.

The compound of the present invention, or pharmaceutically acceptable salts thereof, may be prepared by a variety of procedures known in the art, some of which are illustrated in the schemes, preparations, and examples below. The specific synthetic steps for each of the routes described may be combined in different ways, or in conjunction with steps from different schemes, to prepare the compound of Formula I, or pharmaceutically acceptable salt thereof. The products of each step in the schemes below can be recovered by conventional methods, including extraction, evaporation, precipitation, chromatography, filtration, trituration, and crystallization. The reagents and starting materials are readily available to one of ordinary skill in the art. All substituents, unless otherwise specified, are as previously defined. It is understood that these schemes, preparations, and examples are not intended to be limiting to the scope of the invention in any way.

Scheme 1

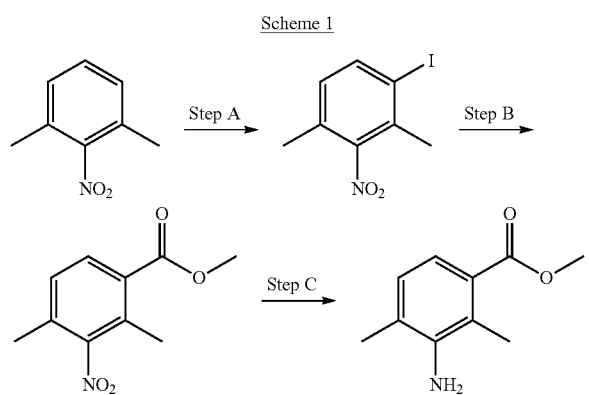

Preparation 1

Methyl 3-amino-2,4-dimethyl-benzoate

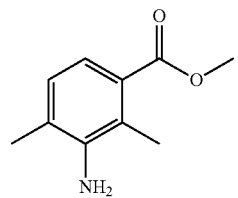

Scheme 1, Step A.

To 1,3-dimethyl-2-nitro-benzene (68.5 g, 453.2 mmol) is added sulfuric acid (27.2 mL, 510 mmol), acetic acid (543.8 mL, 9.49 mol), iodine (46 g, 181.3 mmol) and $HIO_4$ (91.9 g, 403.3 mmol). The reaction is heated to 90° C. for 7 days. The reaction mixture is cooled to ambient temperature, and water (500 mL) is added. The resulting solid is collected by filtration and washed with cold water. The solid is dried under reduced pressure at 45° C. overnight to afford 1-iodo-2,4-dimethyl-3-nitro-benzene as a yellow solid (119 g, 95%). $^1$H NMR (300.16 MHz, CDCl3): δ 7.80 (d, J=8.2 Hz, 1H), 6.85 (d, J=8.2 Hz, 1H), 2.37 (s, 3H), 2.23 (s, 3H).

Scheme 1, Step B.

To a 2 L Parr autoclave with mechanical stirring is added 1-iodo-2,4-dimethyl-3-nitro-benzene (70 g, 252.7 mmol), $Pd(OAc)_2$ (2.8 g, 12.6 mmol), 1,4-bis(diphenylphosphino)butane (6.5 g, 15.2 mmol), acetonitrile (462 mL), triethylamine (88.2 mL), and MeOH (280 mL). The Parr autoclave is sealed, purged, and pressurized with CO to 551.6 kPa (80 psig). The mixture is heated to 100° C. for 2 hours. The mixture is cooled to ambient temperature and then vented. The mixture is then concentrated to dryness under reduced pressure. EtOAc (300 mL) and water (300 mL) are added. The layers are separated, and the aqueous layer discarded. The organic layer is dried over $MgSO_4$, filtered, and concentrated to dryness to afford methyl 2,4-dimethyl-3-nitro-benzoate as a red oil that crystallizes upon standing (52 g, 98%). $^1$H NMR (300.13 MHz, $CDCl_3$): δ 7.89 (d, J=8.2 Hz, 1H), 7.19 (d, J=8.2 Hz, 1H), 3.91 (s, 3H), 2.49 (s, 3H), 2.33 (s, 3H).

Scheme 1, Step C.

To a solution of methyl 2,4-dimethyl-3-nitro-benzoate (37 g, 176.9 mmol) in MeOH (370 mL), 10% palladium on carbon 50% wet (5.6 g) is added. The reaction is bubbled with hydrogen and placed under a hydrogen atmosphere for 6 days. The mixture is filtered through diatomaceous earth, and the filtrate is evaporated to dryness. The resulting residue is purified by silica gel flash chromatography, eluting with 20% EtOAc in hexanes to afford methyl 3-amino-2,4-dimethyl-benzoate as a yellow oil (20.5 g, 65%). Mass spectrum (m/z): 180.1 $(M+H)^+$.

Scheme 2

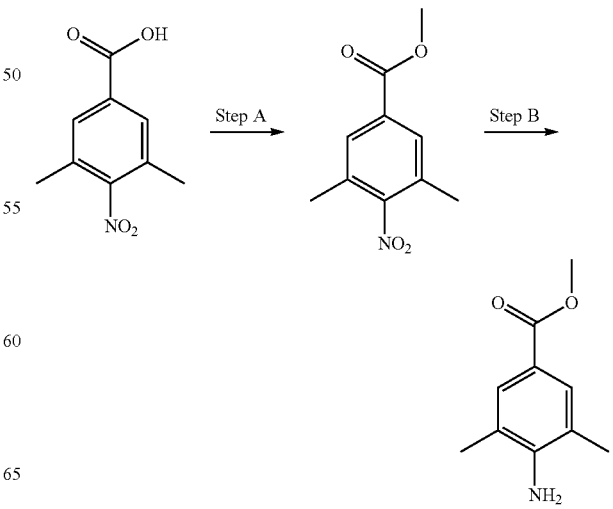

Preparation 2

Methyl 4-amino-3,5-dimethyl-benzoate

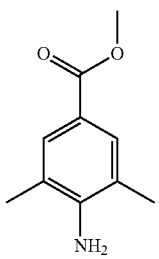

Scheme 2, Step A.

To a solution of 3,5-dimethyl-4-nitro-benzoic acid (10.0 g, 0.0512 mol) in MeOH (150 mL) is added thionyl chloride (10 ml) at 0° C., and the reaction is heated to 80° C. After 16 h, the reaction mixture is cooled to room temperature, and solvent is removed under reduced pressure. The residue is diluted with water (50 ml), brought to pH 7-8 with saturated NaHCO$_3$ solution, and extracted with EtOAc (2×120 mL). The organic layers are combined and dried over anhydrous sodium sulfate. The solvent is removed under reduced pressure to afford methyl 3,5-dimethyl-4-nitro-benzoate as a light yellow solid (10.71 g, 98.3%). $^1$H NMR (400 MHz, DMSO): δ 7.83 (s, 2H), 3.88 (s, 3H), 2.30 (s, 6H).

Scheme 2, Step B.

To a solution of methyl 3,5-dimethyl-4-nitrobenzoate (10.0 g, 0.0478 mol) in MeOH (100 mL), iron powder (15.7 g, 0.2869 mol) and 37% HCl (1.72 g, 0.0478 mol) are added at 0° C. The reaction mixture is heated at 80° C. for 16 hours. The mixture is cooled to room temperature, filtered through diatomaceous earth, and washed with MeOH. The filtrate is concentrated to afford the title compound as brown solid (7.8 g, 99%). Mass spectrum (m/z): 180.2 (M+H)$^+$.

Scheme 3

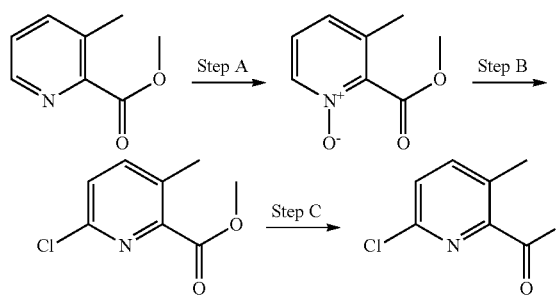

Preparation 3

6-Chloro-3-methyl-pyridine-2-carboxylic acid

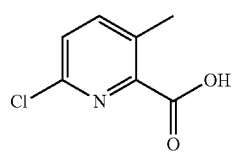

Scheme 3, Step A.

To a solution of methyl 3-methylpyridine-2-carboxylate (13.0 g, 0.086 mol) in CH$_2$Cl$_2$ (130 mL) is added meta-chloroperoxybenzoic acid (89.05 g, 0.258 mol, 50% w/w) portionwise at 0° C. The reaction mixture is stirred for 15 minutes at 0° C. and then gradually warmed to ambient temperature. After 16 hours, saturated NaHCO$_3$ solution (100 mL) is added. The mixture is stirred for 30 minutes and is extracted with CH$_2$Cl$_2$. The combined organic layers are washed with 0.5M NaOH aqueous solution (2×50 mL), dried over sodium sulfate, filtered, and concentrated under reduced pressure to give methyl 3-methyl-1-oxido-pyridin-1-ium-2-carboxylate as an off-white solid (13.0 g, 89.9%). The residue is used in the next step without further purification. Mass spectrum (m/z): 168.2 (M+H)$^+$.

Scheme 3, Step B.

POCl$_3$ (30.0 mL) is added slowly to methyl 3-methyl-1-oxido-pyridin-1-ium-2-carboxylate (13.0 g, 0.077 mol) at 0° C. over 30 minutes. The reaction mixture is stirred for 15 minutes at 0° C. and then gradually warmed to ambient temperature. After 16 hours, the reaction mixture is cooled to 0° C. and excess POCl$_3$ is removed under reduced pressure. The crude residue is then quenched by addition of ice and diluted with water and CH$_2$Cl$_2$ (50 mL). The organic layer is washed sequentially with saturated NaHCO$_3$ solution, water, and brine; dried over sodium sulfate; filtered; and concentrated under reduced pressure. The crude product is purified by silica gel flash chromatography, eluting 5-10% EtOAc in hexanes to afford methyl 6-chloro-3-methyl-pyridine-2-carboxylate as a white solid (3.00 g, 20.9%). Mass spectrum (m/z): 186.2 (M+H)$^+$.

Scheme 3, Step C.

A solution of aqueous 2N NaOH (5 ml) is added to a stirred solution of methyl 6-chloro-3-methyl-pyridine-2-carboxylate (0.500 g, 2.702 mmol) in THF (10 mL) at 0° C. The mixture is heated at 50° C. for 2 hours. The reaction mixture is acidified with aqueous citric acid solution and extracted with EtOAc (2×10 ml). The combined organic layers are dried over sodium sulfate, filtered, and concentrated under reduced pressure to give the title compound as an off-white solid (0.45 g, 97%). The residue is used in next step without further purification. Mass spectrum (m/z): 172.0 (M+H)$^+$.

Scheme 4

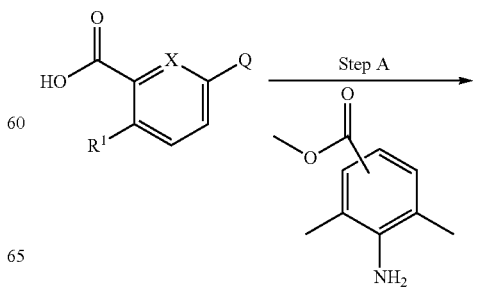

-continued

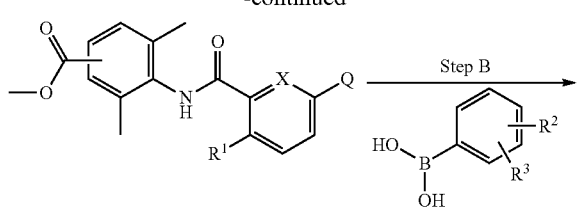

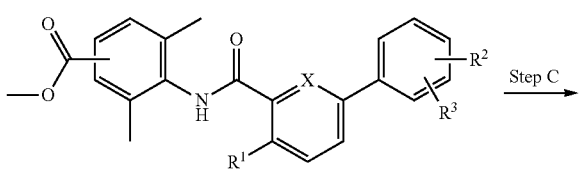

Q = Cl or Br

Preparation 4

Methyl 3-[(5-bromo-2-methyl-benzoyl)amino]-2,4-dimethyl-benzoate

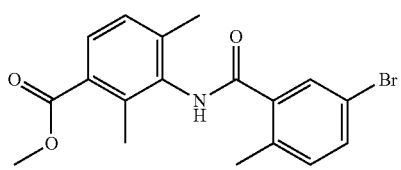 [SMILES: COC(=O)c1ccc(C)c(NC(=O)c2cc(Br)ccc2C)c1C]

Scheme 4, Step A.

To a solution of 5-bromo-2-methyl-benzoic acid (1.0 g, 4.7 mmol) in THF (5.0 ml), $CH_2Cl_2$ (5.0 ml) and DMF (50.0 μl, 646.6 μmoles) is added dropwise oxalyl chloride (2.6 ml, 5.1 mmoles) at 0° C. The reaction mixture is allowed to warm gradually to ambient temperature. After 2 hours, the solvent is removed under reduced pressure. The residue is diluted with $CH_2Cl_2$ (5 ml), and the mixture is cooled to 0° C. Methyl 3-amino-2,4-dimethylbenzoate (957.9 mg, 4.70 mmol) is added, followed by N,N-dimethylpyridin-4-amine (28.4 mg, 0.232 mmoles) and pyridine (1.1 ml, 14.0 mmoles). The cooling bath is removed, and the clear solution is allowed to warm to ambient temperature. After 2 hours, the solution is concentrated. The residue is diluted with EtOAc and washed sequentially with 1N HCl, saturated solution of sodium bicarbonate, and brine. The organic layer is dried over anhydrous $Na_2SO_4$, filtered, and concentrated under reduced pressure. The residue is triturated with 30% EtOAc in Hexanes and the solids are filtered to provide the title compound (680.0 mg; 38.9%). Mass spectrum (m/z): 376.0 $(M+H)^+$.

The following compound is prepared essentially by the method above (Scheme 4, step A), using the appropriate carboxylic acid and amine:

| Prep. | Chemical Name | Structure | MS (m/z) |
|---|---|---|---|
| 5 | Methyl 4-[(5-bromo-2-methyl-benzoyl)amino]-3,5-dimethyl-benzoate | 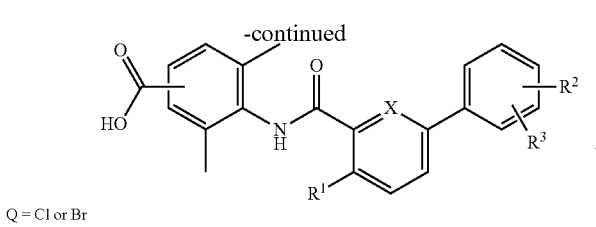 | 376.0 $(M + H)^+$ |

Preparation 6

Methyl 3-[[5-[3-(hydroxymethyl)phenyl]-2-methyl-benzoyl]amino]-2,4-dimethyl-benzoate

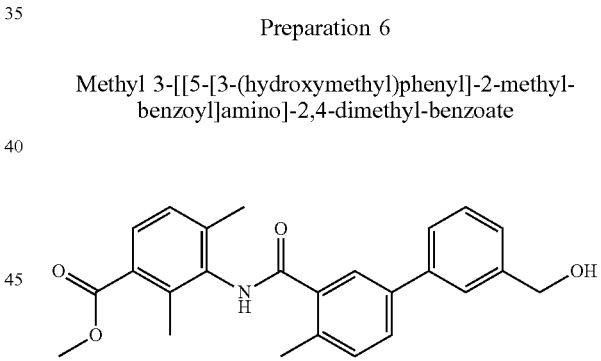

Scheme 4, Step B.

To a solution of methyl 3-[(5-bromo-2-methyl-benzoyl)amino]-2,4-dimethyl-benzoate (0.18 g, 0.478 mmol) in 1,4-dioxane (3.0 ml) and $H_2O$ (0.3 ml) is added (3-(hydroxymethyl)phenyl)boronic acid (87.2 mg, 0.574 mmol) followed by $K_2CO_3$ (132.2 mg, 0.956 mmol) and $PdCl_2$(dppf).$CH_2Cl_2$ (19.5 mg, 0.024 mmol). The reaction mixture is purged with argon for 5 minutes and then heated at 110° C. After 2 hours, the reaction is cooled to room temperature, diluted with water, and extracted with EtOAc. The combined organic layers are dried over sodium sulfate, filtered, and concentrated. The residue is purified by silica gel flash chromatography using 40% EtOAc in hexane. The product is triturated with TBME and filtered to afford the title compound (0.105 g, 54.4%). Mass spectrum (m/z): 404.2 $(M+H)^+$.

The following compounds are prepared essentially by the method above, using the appropriate carboxylic ester and boronic acid:

| Prep. | Chemical Name | Structure | MS (m/z) |
|---|---|---|---|
| 7 | Methyl 3-[[5-[3-(2-hydroxyethyl)phenyl]-2-methyl-benzoyl]amino]-2,4-dimethyl-benzoate | 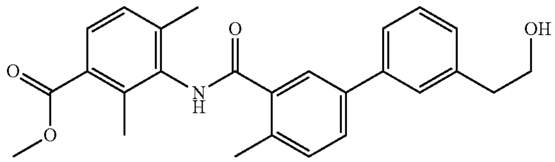 [SMILES: COC(=O)c1ccc(C)c(NC(=O)c2cc(-c3cccc(CCO)c3)ccc2C)c1C] | 418.2 (M + H)+ |
| 8 | Methyl 4-[[5-[3-(hydroxymethyl)phenyl]-2-methyl-benzoyl]amino]-3,5-dimethyl-benzoate | 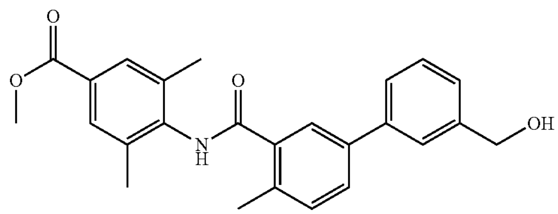 [SMILES: COC(=O)c1cc(C)c(NC(=O)c2cc(-c3cccc(CO)c3)ccc2C)c(C)c1] | 404.2 (M + H)+ |
| 9 | Methyl 4-[[5-[3-(2-hydroxyethyl)phenyl]-2-methyl-benzoyl]amino]-3,5-dimethyl-benzoate | 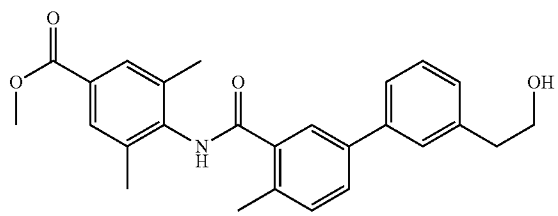 [SMILES: COC(=O)c1cc(C)c(NC(=O)c2cc(-c3cccc(CCO)c3)ccc2C)c(C)c1] | 418.2 (M + H)+ |
| 10 | Methyl 3-[[5-[3-(hydroxymethyl)phenyl]-2-(trifluoromethyl)benzoyl]amino]-2,4-dimethyl-benzoate | 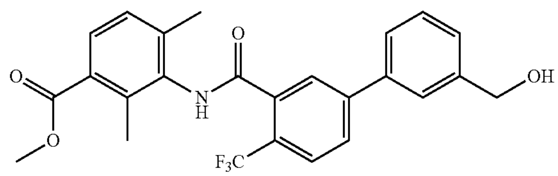 [SMILES: COC(=O)c1ccc(C)c(NC(=O)c2cc(-c3cccc(CO)c3)ccc2C(F)(F)F)c1C] | 458.2 (M + H)+ |
| 11 | Methyl 3-[[5-phenyl-2-(trifluoromethyl)benzoyl]amino]-2,4-dimethyl-benzoate | 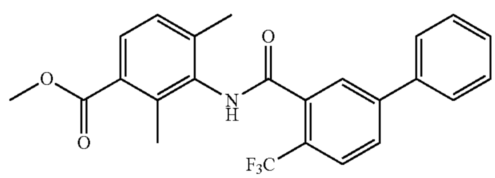 [SMILES: COC(=O)c1ccc(C)c(NC(=O)c2cc(-c3ccccc3)ccc2C(F)(F)F)c1C] | 428.2 (M + H)+ |
| 12 | Methyl 4-[[5-[3-(hydroxymethyl)phenyl]-2-(trifluoromethyl)benzoyl]amino]-3,5-dimethyl-benzoate | 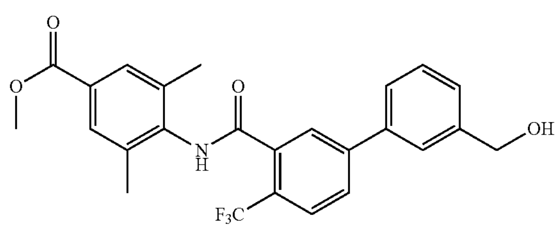 [SMILES: COC(=O)c1cc(C)c(NC(=O)c2cc(-c3cccc(CO)c3)ccc2C(F)(F)F)c(C)c1] | 456.2 (M + H)+ |
| 13 | Methyl 3-[[2-fluoro-5-[3-(hydroxymethyl)phenyl]benzoyl]amino]-2,4-dimethyl-benzoate | 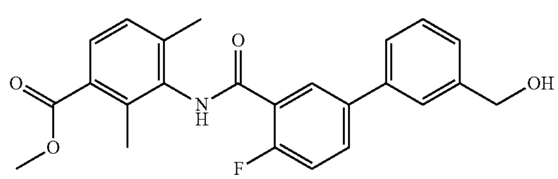 [SMILES: COC(=O)c1ccc(C)c(NC(=O)c2cc(-c3cccc(CO)c3)ccc2F)c1C] | 408.0 (M + H)+ |
| 14 | Methyl 4-[[2-fluoro-5-[3-(hydroxymethyl)phenyl]benzoyl]amino]-3,5-dimethyl-benzoate | 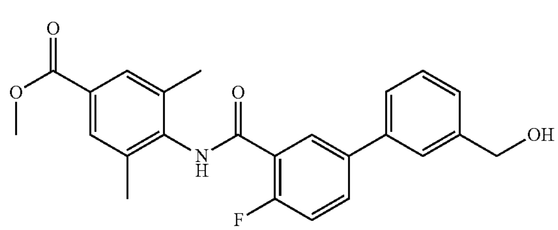 [SMILES: COC(=O)c1cc(C)c(NC(=O)c2cc(-c3cccc(CO)c3)ccc2F)c(C)c1] | 408.4 (M + H)+ |

-continued

| Prep. | Chemical Name | Structure | MS (m/z) |
|---|---|---|---|
| 15 | Methyl 4-[[6-[3-(hydroxymethyl)phenyl]-3-(trifluoromethyl)pyridine-2-carbonyl]amino]-3,5-dimethyl-benzoate | 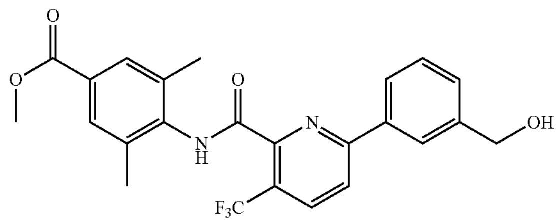 [SMILES: COC(=O)c1cc(C)c(NC(=O)c2nc(-c3cccc(CO)c3)ccc2C(F)(F)F)c(C)c1] | 459.2 (M + H)+ |
| 16 | Methyl 3-[[6-[3-(hydroxymethyl)phenyl]-3-(trifluoromethyl)pyridine-2-carbonyl]amino]-2,4-dimethyl-benzoate | 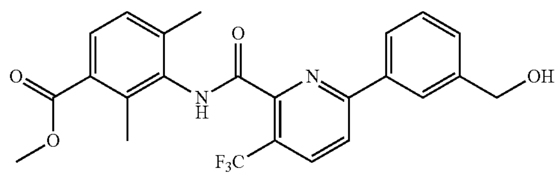 [SMILES: COC(=O)c1ccc(C)c(NC(=O)c2nc(-c3cccc(CO)c3)ccc2C(F)(F)F)c1C] | 459.0 (M + H)+ |

EXAMPLE 1

3-[[5-[3-(Hydroxymethyl)phenyl]-2-methyl-benzoyl]amino]-2,4-dimethyl-benzoic acid

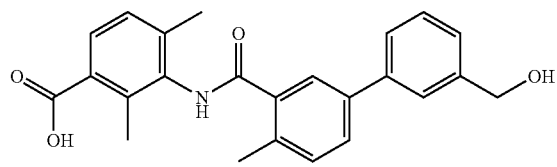 [SMILES: Cc1ccc(-c2cccc(CO)c2)cc1C(=O)Nc1c(C)ccc(C(=O)O)c1C]

Scheme 4, Step C.

Aqueous 1N NaOH (0.5 ml) is added to a stirred solution of methyl 3-[[5-[3-(hydroxymethyl)phenyl]-2-methyl-benzoyl]amino]-2,4-dimethyl-benzoate (0.102 g, 0.252 mmol) in THF (2.0 ml) and MeOH (1.0 ml). After heating at 50° C. for 12 hours, the reaction mixture is acidified to pH 1-2 with aqueous 1N HCl solution. The resulting precipitate is filtered, washed with water, and dried at 40° C. in a vacuum oven for 1 hour to give the title compound as a white solid (95.0 mg, 96.5%). Mass spectrum (m/z): 390.2 (M+H)+.

The following compounds are prepared essentially by the method described in Example 1 from the corresponding carboxylic esters described in the preparations:

| Example | Chemical Name | Structure | MS (m/z) |
|---|---|---|---|
| 2 | 3-[[5-[3-[2-hydroxyethyl)phenyl]-2-methyl-benzoyl]amino]-2,4-dimethyl-benzoic acid | 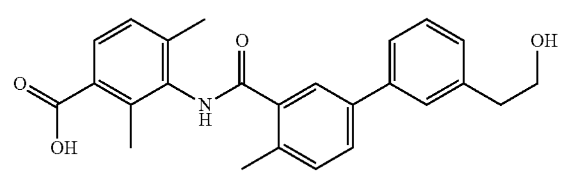 [SMILES: Cc1ccc(-c2cccc(CCO)c2)cc1C(=O)Nc1c(C)ccc(C(=O)O)c1C] | 404.5 (M + H)+ |
| 3 | 4-[[5-[3-(hydroxymethyl)phenyl]-2-methyl-benzoyl]amino]-3,5-dimethyl-benzoic acid | 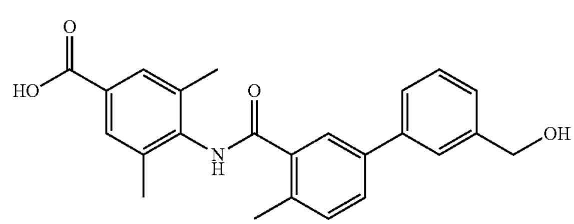 [SMILES: Cc1ccc(-c2cccc(CO)c2)cc1C(=O)Nc1c(C)cc(C(=O)O)cc1C] | 390.2 (M + H)+ |
| 4 | 4-[[5-[3-(2-hydroxyethyl)phenyl]-2-methyl-benzoyl]amino]-3,5-dimethyl-benzoic acid | 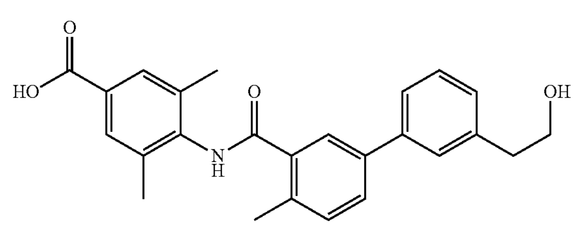 [SMILES: Cc1ccc(-c2cccc(CCO)c2)cc1C(=O)Nc1c(C)cc(C(=O)O)cc1C] | 404.2 (M + H)+ |

| Example | Chemical Name | Structure | MS (m/z) |
|---|---|---|---|
| 5 | 3-[[5-[3-(hydroxymethyl)phenyl]-2-(trifluoromethyl)benzoyl]amino]-2,4-dimethyl-benzoic acid | 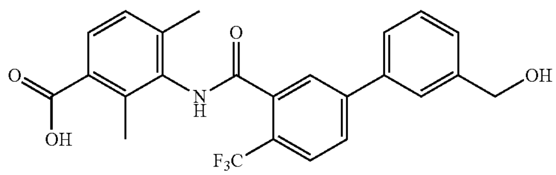 [SMILES: Cc1ccc(C(=O)O)c(C)c1NC(=O)c1cc(-c2cccc(CO)c2)ccc1C(F)(F)F] | 444.2 (M + H)+ |
| 6 | 3-[[5-phenyl-2-(trifluoromethyl)benzoyl]amino]-2,4-dimethyl-benzoic acid | 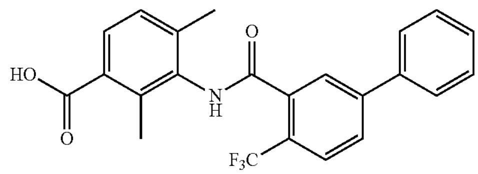 [SMILES: Cc1ccc(C(=O)O)c(C)c1NC(=O)c1cc(-c2ccccc2)ccc1C(F)(F)F] | 414.2 (M + H)+ |
| 7 | 3-[[6-[3-(Methoxymethyl)phenyl]-3-methyl-pyridine-2-carbonyl]amino]-2,4-dimethyl-benzoic acid | 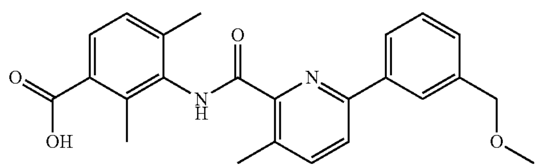 [SMILES: COCc1cccc(-c2ccc(C)c(C(=O)Nc3c(C)ccc(C(=O)O)c3C)n2)c1] | 405.2 (M + H)+ |
| 8 | 3-[[6-[3-(2-Hydroxyethyl)phenyl]-3-methyl-pyridine-2-carbonyl]amino]-2,4-dimethyl-benzoic acid | 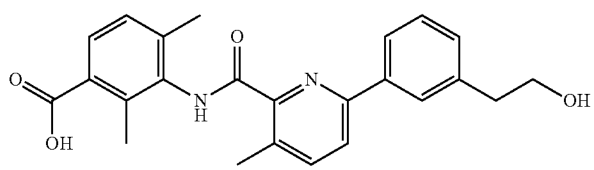 [SMILES: Cc1ccc(-c2cccc(CCO)c2)nc1C(=O)Nc1c(C)ccc(C(=O)O)c1C] | 405.2 (M + H)+ |
| 9 | 4-[[6-[3-(Hydroxymethyl)phenyl]-3-methyl-pyridine-2-carbonyl]amino]-3,5-dimethyl-benzoic acid | 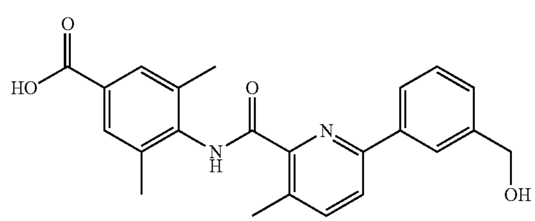 [SMILES: Cc1ccc(-c2cccc(CO)c2)nc1C(=O)Nc1c(C)cc(C(=O)O)cc1C] | 391.1 (M + H)+ |
| 10 | 4-[[6-[3-(Hydroxymethyl)phenyl]-3-(trifluoromethyl)pyridine-2-carbonyl]amino]-3,5-dimethyl-benzoic acid | 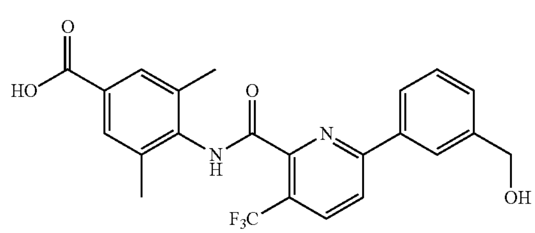 [SMILES: Cc1cc(C(=O)O)cc(C)c1NC(=O)c1nc(-c2cccc(CO)c2)ccc1C(F)(F)F] | 445.2 (M + H)+ |
| 11 | 3-[[6-[3-(Hydroxymethyl)phenyl]-3-(trifluoromethyl)pyridine-2-carbonyl]amino]-2,4-dimethyl-benzoic acid | 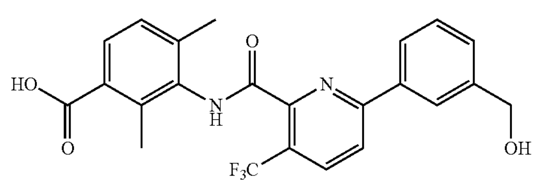 [SMILES: Cc1ccc(C(=O)O)c(C)c1NC(=O)c1nc(-c2cccc(CO)c2)ccc1C(F)(F)F] | 445.2 (M + H)+ |

Preparation 17

Methyl 3-[[5-bromo-2-(trifluoromethyl)benzoyl]amino]-2,4-dimethyl-benzoate

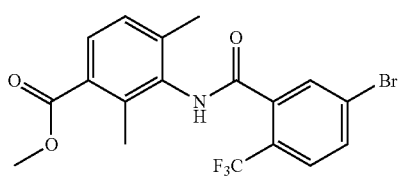 [SMILES: COC(=O)c1ccc(C)c(NC(=O)c2cc(Br)ccc2C(F)(F)F)c1C]

To a solution of 5-bromo-2-(trifluoromethyl)benzoic acid (1.0 g, 3.53 mmol) in CH$_2$Cl$_2$ (6 ml) at room temperature are added methyl 3-amino-2,4-dimethylbenzoate (0.44 g, 2.47 mmol) and triethylamine (1.0 ml, 7.06 mmol). After stirring 10 minutes, 1-propanephosphonic acid cyclic anhydride (50% solution in EtOAc, 5.6 ml, 8.83 mmol) is added via syringe. After 14 hours at ambient temperature, the reaction mixture is diluted with CH$_2$Cl$_2$ and washed with water then brine. The organic layer is dried over anhydrous Na$_2$SO$_4$, filtered, and concentrated under reduced pressure. The residue is purified by silica gel flash chromatography) using 20% EtOAc in hexanes to give the title compound as white solid (0.6 g, 39%). Mass spectrum (m/z): 430.0 (M+H)$^+$.

The following compound is prepared essentially by the method described in preparation 17 above, using the appropriate carboxylic acid and amine:

| Prep. | Chemical Name | Structure | MS (m/z) |
|---|---|---|---|
| 18 | Methyl 4-[[5-bromo-2-(trifluoromethyl)benzoyl]amino]-3,5-dimethyl-benzoate | 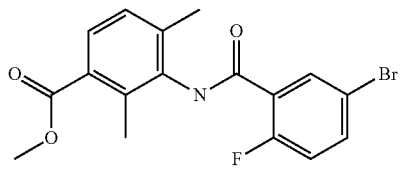 | 430.0 (M + H)$^+$ |

EXAMPLE 12

4-[[5-[3-(Hydroxymethyl)phenyl]-2-(trifluoromethyl)benzoyl]amino]-3,5-dimethyl-benzoic acid

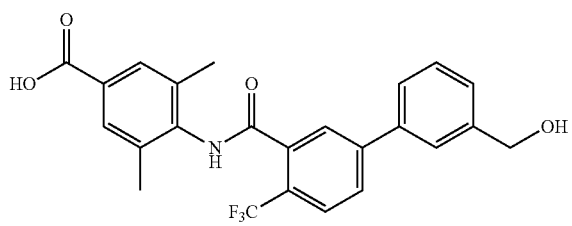 [SMILES: Cc1cc(C(=O)O)cc(C)c1NC(=O)c1cc(-c2cccc(CO)c2)ccc1C(F)(F)F]

Scheme 4, Step C.

Aqueous 2N NaOH (2.0 ml) is added to a stirred solution of methyl 4-[[5-[3-(hydroxymethyl)phenyl]-2-(trifluoromethyl)benzoyl]amino]-3,5-dimethyl-benzoate (0.09 g, 0.197 mmol) in THF (8.0 ml) and MeOH (2.0 ml). After stirring at room temperature for 12 hours, the reaction mixture is concentrated and purified by preparative HPLC using 0.1% TFA in water/acetonitrile (10-90%) to give the title compound (25.0 mg, 29.7%). Mass spectrum (m/z): 444.2 (M+H)$^+$.

Preparation 19

Methyl 3-[(5-bromo-2-fluoro-benzoyl)amino]-2,4-dimethyl-benzoate

To a solution of 5-bromo-2-fluoro-benzoic acid (0.5 g, 2.28 mol) in CH$_2$Cl$_2$ (5.0 ml) at room temperature are added methyl 3-amino-2,4-dimethylbenzoate (0.38 g, 2.17 mol) and DIEA (1.17 g, 9.13 mol). After stirring 10 minutes, 1-propanephosphonic acid cyclic anhydride (50% solution in EtOAc, 2.0 ml, 3.42 mol) is added via syringe. After 16 hours at ambient temperature, the reaction mixture is diluted with water and extracted with CH$_2$Cl$_2$. The combined organic layers are dried over sodium sulfate, filtered, and concentrated under reduced pressure. The residue is purified by silica gel flash chromatography using 22% EtOAc to give the title compound as off white solid (0.80 g, 93%). Mass spectrum (m/z): 380.0 (M+H)$^+$.

The following compound is prepared essentially by the method described above in preparation 19, using the appropriate carboxylic acid and amine:

| Prep. | Chemical Name | Structure | MS (m/z) |
|---|---|---|---|
| 20 | Methyl 4-[(5-bromo-2-fluoro-benzoyl)amino]-3,5-dimethyl-benzoate | 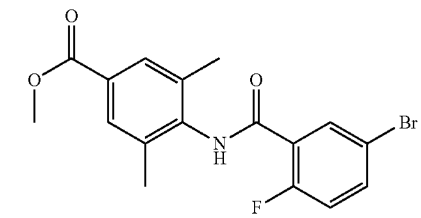 [SMILES: COC(=O)c1cc(C)c(NC(=O)c2cc(Br)ccc2F)c(C)c1] | 380.0 (M + H)⁺ |
| 21 | Ethyl 4-[(6-chloro-3-methyl-pyridine-2-carbonyl)amino]-3,5-dimethyl-benzoate | 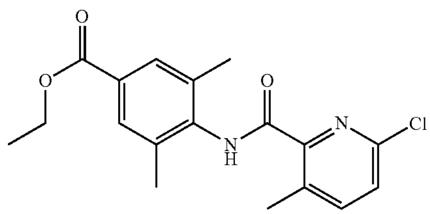 [SMILES: CCOC(=O)c1cc(C)c(NC(=O)c2nc(Cl)ccc2C)c(C)c1] | 347.2 (M + H)⁺ |
| 22 | Methyl 4-[(6-chloro-3-methyl-pyridine-2-carbonyl)amino]-3,5-dimethyl-benzoate | 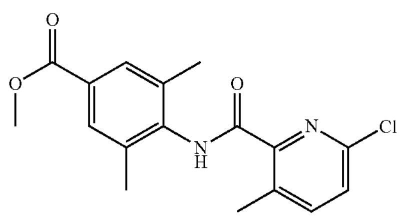 [SMILES: COC(=O)c1cc(C)c(NC(=O)c2nc(Cl)ccc2C)c(C)c1] | 333.0 (M + H)⁺ |

EXAMPLE 13

3-[[2-Fluoro-5-[3-(hydroxymethyl)phenyl]benzoyl]amino]-2,4-dimethyl-benzoic acid

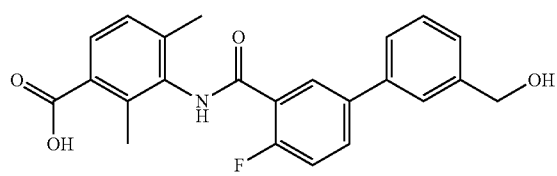 [SMILES: Cc1ccc(C(=O)O)c(C)c1NC(=O)c1cc(-c2cccc(CO)c2)ccc1F]

Aqueous 4N NaOH (5.0 ml) is added to a stirred solution of methyl 3-[[2-fluoro-5-[3-(hydroxymethyl)phenyl]benzoyl]amino]-2,4-dimethyl-benzoate (0.30 g, 0.737 mmol) in THF (5.0 ml) and t-butanol (5.0 ml). After heating at 60° C. for 16 hours, the reaction mixture is acidified to pH 1-2 with aqueous 1N HCl solution and extracted with CH₂Cl₂. The combined organic layers are dried over sodium sulfate, filtered, and concentrated under reduced pressure to give the title compound as off-white solid (0.19 g, 65.5%). Mass spectrum (m/z): 392.1 (M−H)⁺.

The following compounds are prepared essentially by the method of Example 13 above, using the appropriate carboxylic ester:

| Example | Chemical Name | Structure | MS (m/z) |
|---|---|---|---|
| 14 | 4-[[2-Fluoro-5-[3-(hydroxymethyl)phenyl]benzoyl]amino]-3,5-dimethyl-benzoic acid | 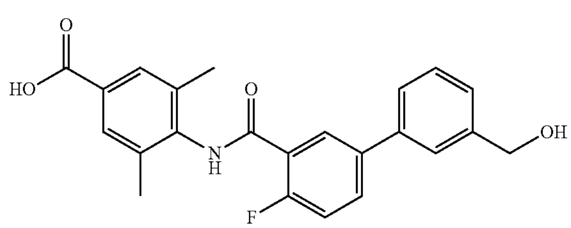 [SMILES: Cc1cc(C(=O)O)cc(C)c1NC(=O)c1cc(-c2cccc(CO)c2)ccc1F] | 392.1 (M − H)⁺ |

Scheme 5

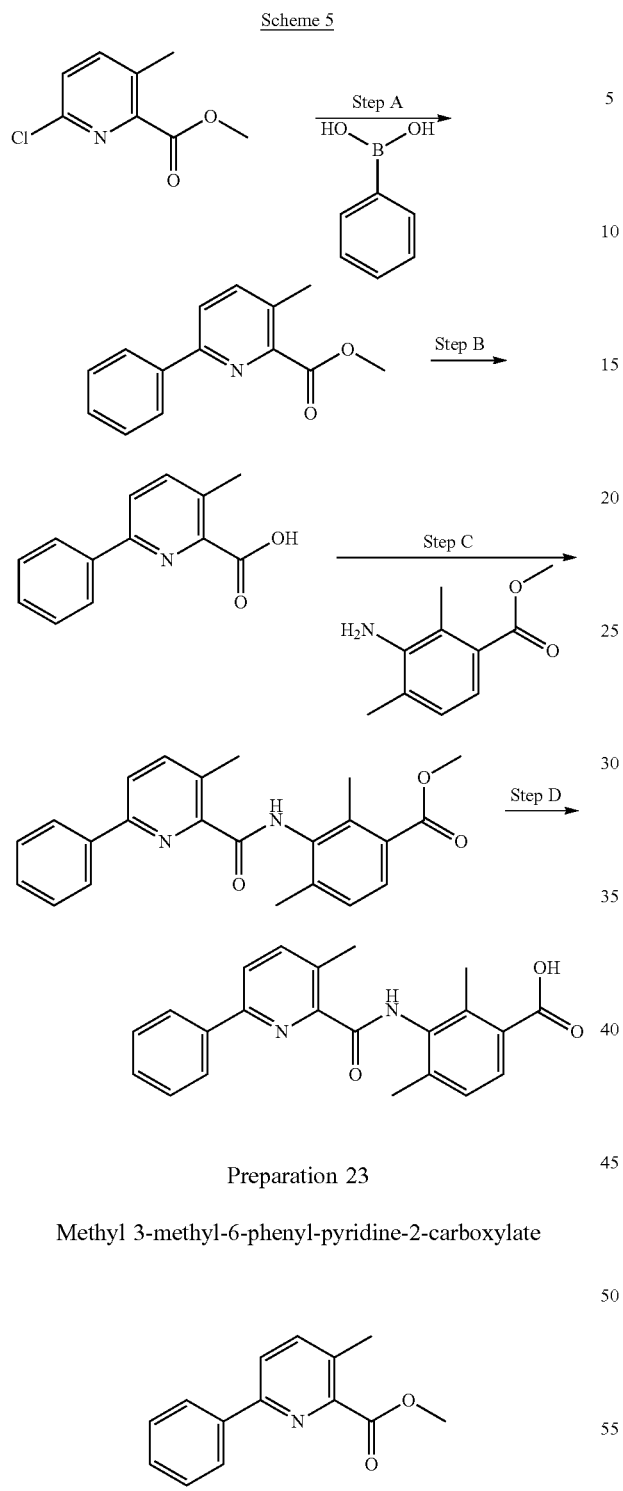

Preparation 23

Methyl 3-methyl-6-phenyl-pyridine-2-carboxylate

Scheme 5, Step A.

To a solution of methyl 6-chloro-3-methyl-pyridine-2-carboxylate (1.0 g, 5.39 mmol), phenylboronic acid (0.79 g, 6.47 mmol) in 1,4-dioxane (17 mL) and water (3.0 ml) is added K₂CO₃ (1.64 g, 11.8 mmol). The reaction mixture is purged with argon for 15 min and PdCl₂(dppf).CH₂Cl₂ (131.9 mg, 0.162 mmol) is added. The mixture is purged again with argon for 5 min. After heating at 110° C. for 2 h, the reaction mixture is cooled to room temperature, diluted with water, and extracted with EtOAc. The combined organic layers are dried over anhydrous magnesium sulfate, filtered, and concentrated under reduced pressure. The crude residue is purified by silica gel flash column chromatography using 0-20% EtOAc in hexanes t to afford the title compound as a clear oil (985.0 mg, 80.5%). Mass spectrum (m/z): 228.0 (M–H)⁺.

Preparation 24

3-Methyl-6-phenyl-pyridine-2-carboxylic acid

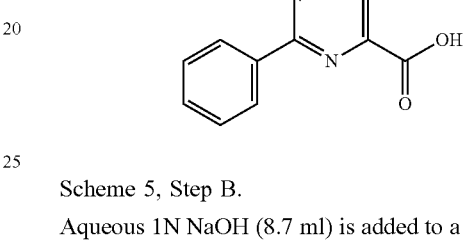

Scheme 5, Step B.

Aqueous 1N NaOH (8.7 ml) is added to a stirred solution of methyl 6-chloro-3-methyl-pyridine-2-carboxylate (985 mg, 4.33 mmol) in THF (5.0 ml) and MeOH (5.0 ml). The mixture is stirred at ambient temperature for 3 hours, concentrated under reduced pressure, and acidified with 1N HCl to pH 3. The resulting precipitate is isolated by filtration, washed with water, and dried in a vacuum oven at 40° C. to give the title compound (685.0 mg, 74.1%). Mass spectrum (m/z): 214.0 (M–H)⁺.

Preparation 25

Methyl 2,4-dimethyl-3-[(3-methyl-6-phenyl-pyridine-2-carbonyl)amino]benzoate

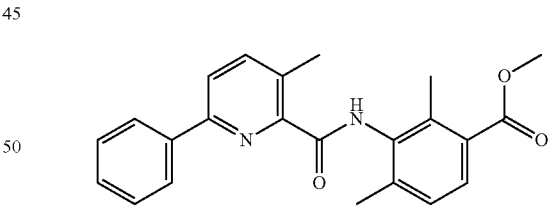

Scheme 5, Step C.

To a solution of 3-methyl-6-phenyl-pyridine-2-carboxylic acid (342.0 mg, 1.60 mmol) in CH₂Cl₂ (8 ml) at room temperature are added methyl 3-amino-2,4-dimethyl-benzoate (287.4 mg, 1.60 mmol) and DIEA (699.3 mg, 4.01 mmol). After stirring for 10 minutes, 1-propanephosphonic acid cyclic anhydride (50% solution in EtOAc, 1.22 g, 1.92 mmol) is added via syringe. After 15 hours at 50° C., the reaction mixture is triturated with CH₂Cl₂/TBME and resulting precipitate is isolated by filtration to give the title compound as a white powder (0.41 g, 68%). Mass spectrum (m/z): 375.2 (M+H)⁺.

EXAMPLE 15

2,4-Dimethyl-3-[(3-methyl-6-phenyl-pyridine-2-carbonyl)amino]benzoic acid

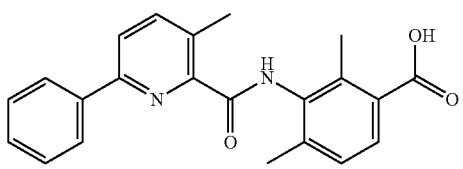 [SMILES: Cc1ccc(-c2ccccc2)nc1C(=O)Nc1c(C)ccc(C(=O)O)c1C]

Scheme 5, Step D.

To a solution of methyl 2,4-dimethyl-3-[(3-methyl-6-phenyl-pyridine-2-carbonyl)amino]benzoate (0.28 g, 0.75 mmol) in THF (3.0 ml), MeOH (3.0 ml), and H₂O (1.0 ml) is added LiOH.H₂O (0.157 g, 3.75 mmol). After heating at 50° C. for 1 hour, the reaction mixture is acidified to pH ~6. The aqueous layer is saturated with solid NaCl and extracted with EtOAc (4×20 mL). The combined organic layers are dried over sodium sulfate, filtered, and concentrated under reduced pressure. The residue is triturated with diethyl ether to afford the title compound as a white solid (0.231 g, 85.7%). Mass spectrum (m/z): 361.2 (M+H)⁺.

Alternative synthesis of 2,4-dimethyl-3-[(3-methyl-6-phenyl-pyridine-2-carbonyl)amino]benzoic acid (Example 15)

vacuum to give 3-methyl-1-oxido-pyridin-1-ium-2-carbonitrile as a yellow solid (16.2 g, 86.7%). Mass spectrum (m/z): 135.0 (M+H)⁺.

Scheme 6, Step B.

To a round bottom flask is added 3-methyl-1-oxo-pyridine-2-carbonitrile (16.2 g, 120.77 mmoles), toluene (8 mL), and phosphoryl chloride (16.83 mL; 181.2 mmoles). The mixture is stirred at 90° C. for 90 minutes, cooled to RT, and added dropwise to aqueous 2M KH₂PO₄ (483 mL; 966 mmoles). The mixture is stirred 30 minutes, and the layers are separated. The organic layer is dried over MgSO₄, filtered, and concentrated to 6-chloro-3-methyl-pyridine-2-carbonitril: Mass spectrum (m/z): 153.0 (M+H)⁺. Phenylboronic acid (17.94 g, 144.9 mmoles), toluene (130 mL), sodium carbonate (190.2 g, 362.31 mmoles), bis(triphenylphosphine)palladium(II) chloride (856 mg; 1.21 mmoles) are added to this crude material. The mixture is stirred at 80° C. for 1 hour and cooled to RT. The layers are separated, and the organic layer is dried over MgSO₄, filtered, and concentrated. The material was purified by silica gel chromatography (400 g ISCO® cartridge) using methylene chloride in hexanes from 20 to 100% to afford 3-methyl-6-phenyl-pyridine-2-carbonitrile (6.7 g, 28.6%). Mass spectrum (m/z): 195.1 (M+H)⁺.

Scheme 6, Step C.

To a pale yellow suspension of 3-methyl-6-phenyl-pyridine-2-carbonitrile (6.10 g, 31.41 mmoles) in ethanol (30 mL) is added aqueous 18N sodium hydroxide (10.7 mL, 188.43 mmoles) and water (10.98 mL). The yellow suspension is heated at 100° C. for 18 h and cooled to 22° C. The mixture is diluted with water (100 mL) and neutralized with Scheme 6

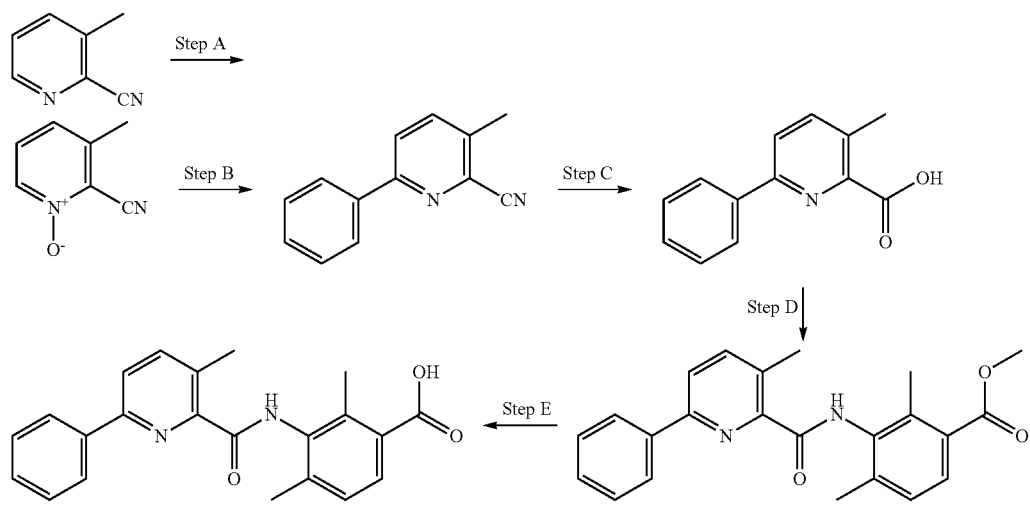

Scheme 6, Step A.

To a round bottom flask containing 3-methylpyridine-2-carbonitrile (16.8 g, 139 mmoles), methylene chloride (70 mL), and methyltrioxorhenium (VII) (1.42 g, 5.57 mmol), hydrogen peroxide (24 mL, 279 mmoles) is added slowly. The mixture was stirred overnight and for an additional 24 hours. Stirring is stopped and the layers are separated. The organic layer is dried over anhydrous magnesium sulfate, filtered, and concentrated. The residue is triturated with TBME (150 mL), and the solid was filtered and dried under aqueous 12M HCl (18.6 mL, 219.8 mmoles) to give a pH ~1. The solid is filtered, washed with water, and dried under vacuum at 45° C. to give 3-methyl-6-phenyl-pyridine-2-carboxylic acid as a white solid (6.50 g, 94.2%). Mass spectrum (m/z): 214.1 (M+H)⁺.

Scheme 6, Step D.

To 3-methyl-6-phenyl-pyridine-2-carboxylic acid (5.52 g, 25.89 mmoles) is added thionyl chloride (18.9 mL, 258.9 mmoles) at 22° C. The yellow solution is stirred at 22° C. for 8 h and concentrated to give 3-methyl-6-phenyl-pyridine-2-carbonyl chloride as a light brown solid (7.0 g, 25 mmoles).

This material is diluted with THF (70 mL) and treated at 22° C. under nitrogen with a solution of methyl 3-amino-2,4-dimethyl-benzoate (4.54 g, 25.32 mmoles) in THF (35 mL). Pyridine (6.1 mL, 75.97 mmoles) is added slowly, and the reaction mixture is stirred for 45 min. The suspension is filtered, the solid is rinsed with EtOAc, and the filtrate is concentrated to a brown oil. The oil is treated with water (50 mL) and placed in an ultrasonic bath for 10 min. The suspension is filtered, and the solid is washed with water and dried to afford methyl 2,4-dimethyl-3-[(3-methyl-6-phenyl-pyridine-2-carbonyl)amino]benzoate as a light brown solid (9.81 g, 95.8%). Mass spectrum (m/z): 375.1 (M+H)$^+$.

Scheme 6, Step E.

To a solution of methyl 2,4-dimethyl-3-[(3-methyl-6-phenyl-pyridine-2-carbonyl)amino]benzoate (9.00 g, 23.80 mmoles) in THF (90 mL) and MeOH (36 mL) is added aqueous 1M NaOH solution (71.4 mL, 71.4 mmoles). The mixture is heated at 50° C. for 4 hours, cooled to 22° C., and concentrated to remove organic solvents. The aqueous residue is diluted with water (50 mL), washed with EtOAc (20 mL), and acidified with 10% aqueous HCl solution (13.5 mL, 40.4 mmoles) to a final pH ~3. The solid is filtered, washed with water, recrystallized from acetone/water, and dried in the vacuum oven at 45° C. for 18 h to afford the title compound as an off-white solid (6.20 g, 72.3%). Mass spectrum (m/z): 361.1 (M+H)$^+$.

Scheme 7

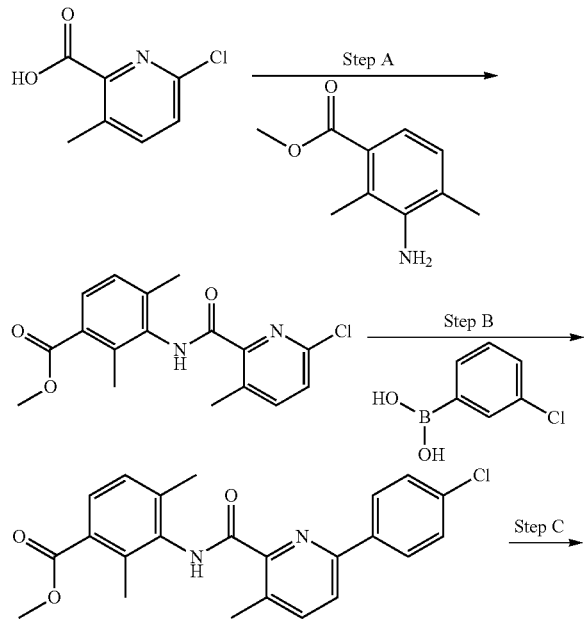

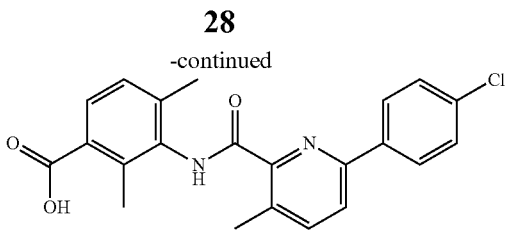

Preparation 26

Methyl 3-[[6-(4-chlorophenyl)-3-methyl-pyridine-2-carbonyl]amino]-2,4-dimethyl-benzoate Scheme 7, Step A.

To a solution of 6-chloro-3-methyl-pyridine-2-carboxylic acid (0.8 g, 4.6 mmol) in CH$_2$Cl$_2$ (4 mL) at room temperature are added methyl 3-amino-2,4-dimethyl-benzoate (0.84 g, 4.6 mmol) and TEA (945.0 mg, 9.3 mmol). After stirring 10 minutes, 1-propanephosphonic acid cyclic anhydride (50% solution in EtOAc, 2.97 g, 9.3 mmol) is added via syringe. After 2 hours at 35° C., the reaction mixture is diluted with saturated NaHCO$_3$ solution and extracted with CH$_2$Cl$_2$. The combined organic layers are dried over sodium sulfate, filtered, and concentrated under reduced pressure. The residue is purified by silica gel flash chromatography, eluting with 10% EtOAc in hexanes to give methyl 3-[(6-chloro-3-methyl-pyridine-2-carbonyl)amino]-2,4-dimethyl-benzoate as a colorless oil (1.1 g, 72%). Mass spectrum (m/z): 333.3 (M+H)$^+$.

Scheme 7, Step B.

To a solution of methyl 3-[(6-chloro-3-methyl-pyridine-2-carbonyl)amino]-2,4-dimethyl-benzoate (230.0 mg, 0.692 mmol) in 1,4-dioxane (5.0 ml) and H$_2$O (1.0 ml) is added (4-chlorophenyl)boronic acid (120.0 mg, 0.761 mmol) followed by Na$_2$CO$_3$ (220.0 mg, 2.08 mmol) and PdCl$_2$(dppf).CH$_2$Cl$_2$ (60.0 mg, 0.069 mmol). The reaction mixture is purged with argon for 5 minutes and then heated at 100° C. After 14 hours, the reaction is cooled to RT, diluted with water, and extracted with EtOAc. The combined organic layers are dried over sodium sulfate, filtered, and concentrated. The residue is purified by silica gel flash chromatography using 50% EtOAc in hexane to afford the title compound (0.17 g, 60.7%).

The following compounds are prepared essentially by the methods described above in preparation 26, using the appropriate carboxylic ester and boronic acid:

| Prep. | Chemical Name | Structure | MS (m/z) |
|---|---|---|---|
| 27 | Methyl 3-[[6-(3-chlorophenyl)-3-methyl-pyridine-2-carbonyl]amino]-2,4-dimethyl-benzoate | 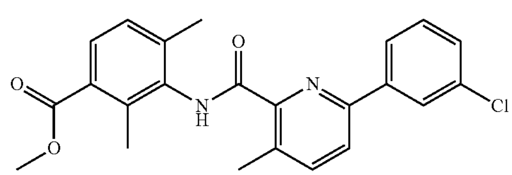 [SMILES: COC(=O)c1ccc(C)c(NC(=O)c2nc(-c3cccc(Cl)c3)ccc2C)c1C] | 409.2 (M + H)$^+$ |

-continued

| Prep. | Chemical Name | Structure | MS (m/z) |
|---|---|---|---|
| 28 | methyl 3-[[6-(1,3-benzodioxol-5-yl)-3-methyl-pyridine-2-carbonyl]amino]-2,4-dimethyl-benzoate | 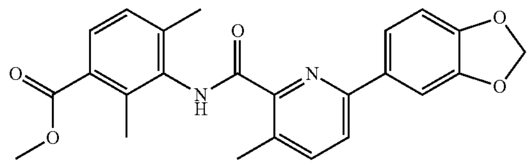 [SMILES: COC(=O)c1ccc(C)c(NC(=O)c2nc(-c3ccc4c(c3)OCO4)ccc2C)c1C] | 419.9 (M + H)+ |
| 29 | Methyl 3-[[6-(3-cyanophenyl)-3-methyl-pyridine-2-carbonyl]amino]-2,4-dimethyl-benzoate | 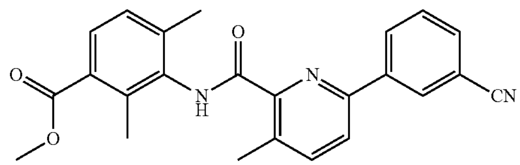 [SMILES: COC(=O)c1ccc(C)c(NC(=O)c2nc(-c3cccc(C#N)c3)ccc2C)c1C] | 400.2 (M + H)+ |
| 30 | Methyl 3-[[6-[3-(hydroxymethyl)phenyl]-3-methyl-pyridine-2-carbonyl]amino]-2,4-dimethyl-benzoate | 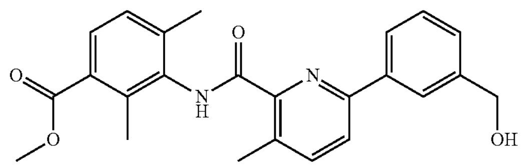 [SMILES: COC(=O)c1ccc(C)c(NC(=O)c2nc(-c3cccc(CO)c3)ccc2C)c1C] | 405.4 (M + H)+ |
| 31 | Methyl 3-[[6-[3-(methoxymethyl)phenyl]-3-methyl-pyridine-2-carbonyl]amino]-2,4-dimethyl-benzoate | 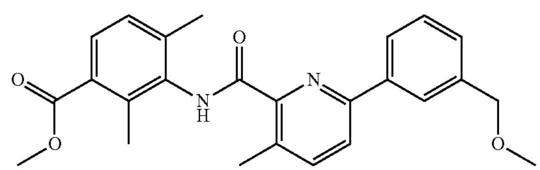 [SMILES: COCc1cccc(-c2ccc(C)c(C(=O)Nc3c(C)ccc(C(=O)OC)c3C)n2)c1] | 419.2 (M + H)+ |
| 32 | Methyl 3-[[6-[4-fluoro-3-(hydroxymethyl)phenyl]-3-methyl-pyridine-2-carbonyl]amino]-2,4-dimethyl-benzoate | 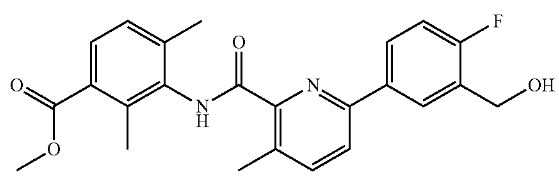 [SMILES: COC(=O)c1ccc(C)c(NC(=O)c2nc(-c3ccc(F)c(CO)c3)ccc2C)c1C] | 423.2 (M + H)+ |
| 33 | Methyl 3-[[6-[3-(2-hydroxyethyl)phenyl]-3-methyl-pyridine-2-carbonyl]amino]-2,4-dimethyl-benzoate | 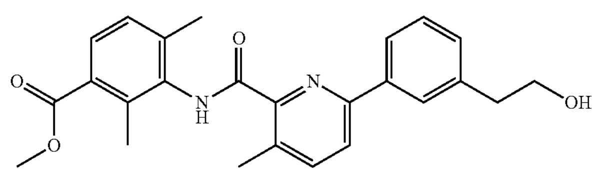 [SMILES: COC(=O)c1ccc(C)c(NC(=O)c2nc(-c3cccc(CCO)c3)ccc2C)c1C] | 419.2 (M + H)+ |
| 34 | Ethyl 4-[[6-[3-(hydroxymethyl)phenyl]-3-methyl-pyridine-2-carbonyl]amino]-3,5-dimethyl-benzoate | 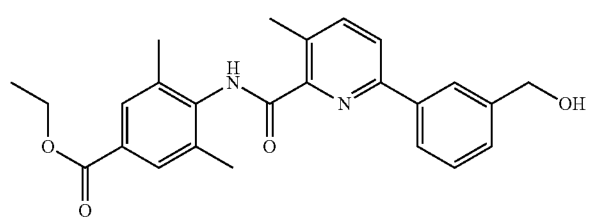 [SMILES: CCOC(=O)c1cc(C)c(NC(=O)c2nc(-c3cccc(CO)c3)ccc2C)c(C)c1] | 419.2 (M + H)+ |
| 35 | Methyl 4-[[6-[4-(hydroxymethyl)phenyl]-3-methyl-pyridine-2-carbonyl]amino]-3,5-dimethyl-benzoate | 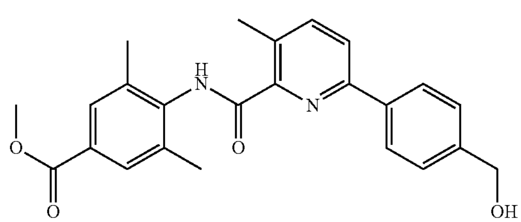 [SMILES: COC(=O)c1cc(C)c(NC(=O)c2nc(-c3ccc(CO)cc3)ccc2C)c(C)c1] | 405.4 (M + H)+ |

| Prep. | Chemical Name | Structure | MS (m/z) |
|---|---|---|---|
| 36 | Methyl 4-[[6-[4-fluoro-3-(hydroxymethyl)phenyl]-3-methyl-pyridine-2-carbonyl]amino]-3,5-dimethyl-benzoate | 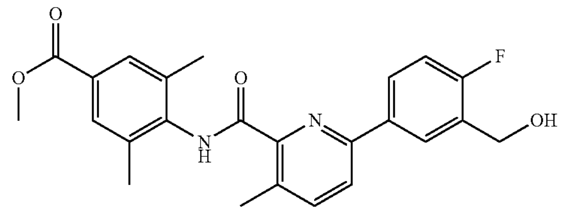 [SMILES: COC(=O)c1cc(C)c(NC(=O)c2nc(-c3ccc(F)c(CO)c3)ccc2C)c(C)c1] | 423.0 (M + H)+ |
| 37 | Methyl 4-[[6-[3-(2-hydroxyethyl)phenyl]-3-methyl-pyridine-2-carbonyl]amino]-3,5-dimethyl-benzoate | 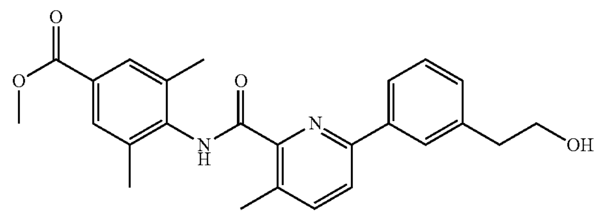 [SMILES: COC(=O)c1cc(C)c(NC(=O)c2nc(-c3cccc(CCO)c3)ccc2C)c(C)c1] | 419.2 (M + H)+ |
| 38 | Methyl 4-[[6-(1,3-benzodioxol-5-yl)-3-methyl-pyridine-2-carbonyl]amino]-3,5-dimethyl-benzoate | 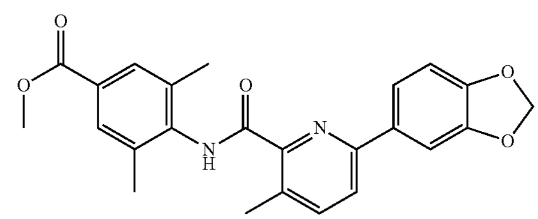 [SMILES: COC(=O)c1cc(C)c(NC(=O)c2nc(-c3ccc4c(c3)OCO4)ccc2C)c(C)c1] | 419.9 (M + H)+ |

EXAMPLE 16

3-[[6-(4-Chlorophenyl)-3-methyl-pyridine-2-carbonyl]amino]-2,4-dimethyl-benzoic acid Scheme 7, Step C.

Aqueous 1N NaOH (2.0 ml) is added to a stirred solution of methyl 3-[[6-(4-chlorophenyl)-3-methyl-pyridine-2-carbonyl]amino]-2,4-dimethyl-benzoate (0.17 g, 0.41 mmol) in THF (8.0 ml) and MeOH (2.0 ml). After heating at 40° C. for 12 hours, the reaction mixture is acidified to pH 1-2 with aqueous 1N HCl solution. The resulting precipitate is filtered, washed with water, and purified by preparative HPLC using 0.1% TFA in water/acetonitrile to give the title compound as a white solid (155 mg, 95.9%). Mass spectrum (m/z): 395.1 (M+H)+.

EXAMPLE 17

3-[[6-(3-Chlorophenyl)-3-methyl-pyridine-2-carbonyl]amino]-2,4-dimethyl-benzoic acid

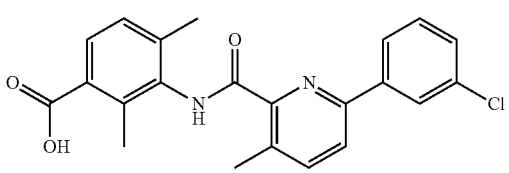 [SMILES: Cc1ccc(-c2cccc(Cl)c2)nc1C(=O)Nc1c(C)ccc(C(=O)O)c1C]

Scheme 7, Step C.

A solution of aqueous 2N NaOH (2.0 ml) is added to a stirred solution of methyl 3-[[6-(1,3-benzodioxol-5-yl)-3-methyl-pyridine-2-carbonyl]amino]-2,4-dimethyl-benzoate (0.17 g, 0.416 mmol) in THF (8.0 ml) and MeOH (2.0 ml) at 0° C. After heating at 60° C. for 2 hours, the reaction mixture is acidified to pH 1-2 with aqueous 1N HCl solution and extracted with $CH_2Cl_2$. The combined organic layers are dried over sodium sulfate, filtered, and concentrated under reduced pressure to give the title compound as a white solid (0.104 g, 64%). Mass spectrum (m/z): 395.2 (M+H)+.

The following compounds are prepared essentially by the method described above in Example 17, using the appropriate carboxylic ester:

| Example | Chemical Name | Structure | MS (m/z) |
|---|---|---|---|
| 18 | 3-[[6-(1,3-Benzodioxol-5-yl)-3-methyl-pyridine-2-carbonyl]amino]-2,4-dimethyl-benzoic acid | 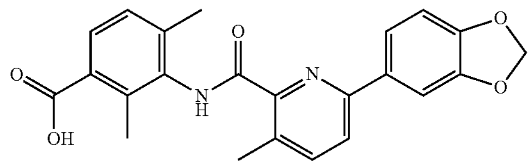 [SMILES: Cc1ccc(-c2ccc3c(c2)OCO3)nc1C(=O)Nc1c(C)ccc(C(=O)O)c1C] | 405.2 (M + H)$^+$ |
| 19 | 3-[[6-(3-Cyanophenyl)-3-methyl-pyridine-2-carbonyl]amino]-2,4-dimethyl-benzoic acid | 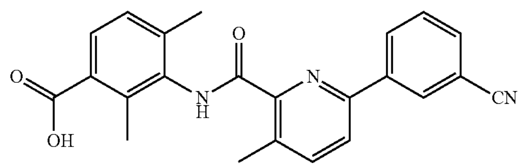 [SMILES: Cc1ccc(-c2cccc(C#N)c2)nc1C(=O)Nc1c(C)ccc(C(=O)O)c1C] | 386.2 (M + H)$^+$ |
| 20 | 3-[[6-[4-Fluoro-3-(hydroxymethyl)phenyl]-3-methyl-pyridine-2-carbonyl]amino]-2,4-dimethyl-benzoic acid | 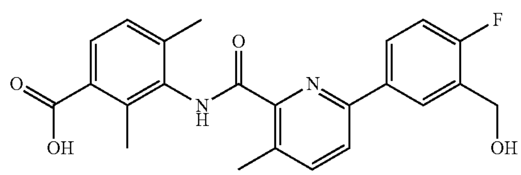 [SMILES: Cc1ccc(-c2ccc(F)c(CO)c2)nc1C(=O)Nc1c(C)ccc(C(=O)O)c1C] | 409.2 (M + H)$^+$ |
| 21 | 4-[[6-[4-fluoro-3-(hydroxymethyl)phenyl]-3-methyl-pyridine-2-carbonyl]amino]-3,5-dimethyl-benzoic acid | 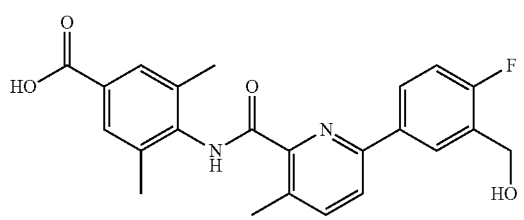 [SMILES: Cc1ccc(-c2ccc(F)c(CO)c2)nc1C(=O)Nc1c(C)cc(C(=O)O)cc1C] | 409.1 (M + H)$^+$ |

EXAMPLE 22

3-[[6-[3-(Hydroxymethyl)phenyl]-3-methyl-pyridine-2-carbonyl]amino]-2,4-dimethyl-benzoic acid

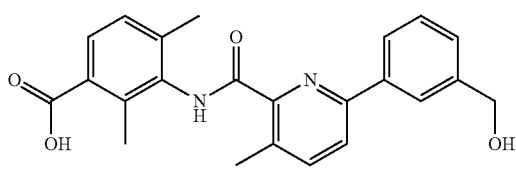 [SMILES: Cc1ccc(-c2cccc(CO)c2)nc1C(=O)Nc1c(C)ccc(C(=O)O)c1C]

Scheme 7, Step C.

A solution of aqueous 2N NaOH (2 ml) is added to a stirred solution of methyl 3-[[6-[3-(hydroxymethyl)phenyl]-3-methyl-pyridine-2-carbonyl]amino]-2,4-dimethyl-benzoate (0.13 g, 0.32 mmol) in THF (10 mL) at 0° C. After heating at 50° C. for 2 hours the reaction mixture is acidified to pH 1-2 with aqueous 1N HCl solution and concentrated. The crude product is purified by preparative HPLC using 10-90% gradient of 5 mM NH$_4$OAc in water/CH$_3$CN to give the title compound as a white solid (0.122 g, 97%). Mass spectrum (m/z): 391.12 (M+H)$^+$.

The following compounds are prepared essentially by the method described above in Example 22, using the appropriate carboxylic ester:

| Example | Chemical Name | Structure | MS (m/z) |
|---|---|---|---|
| 23 | 4-[[6-[4-(Hydroxymethyl)phenyl]-3-methyl-pyridine-2-carbonyl]amino]-3,5-dimethyl-benzoic acid | 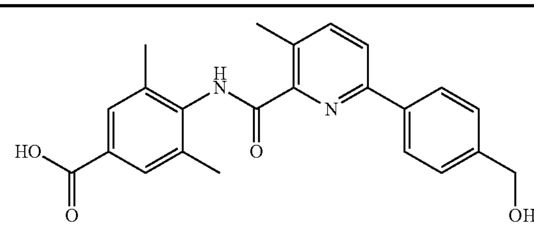 | 391.1 (M + H)$^+$ |

| Example | Chemical Name | Structure | MS (m/z) |
|---|---|---|---|
| 24 | 4-[[6-[3-(2-Hydroxyethyl)phenyl]-3-methyl-pyridine-2-carbonyl]amino]-3,5-dimethyl-benzoic acid | 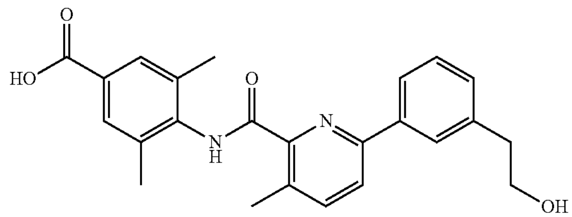 [SMILES: Cc1ccc(-c2cccc(CCO)c2)nc1C(=O)Nc1c(C)cc(C(=O)O)cc1C] | 405.2 (M + H)+ |

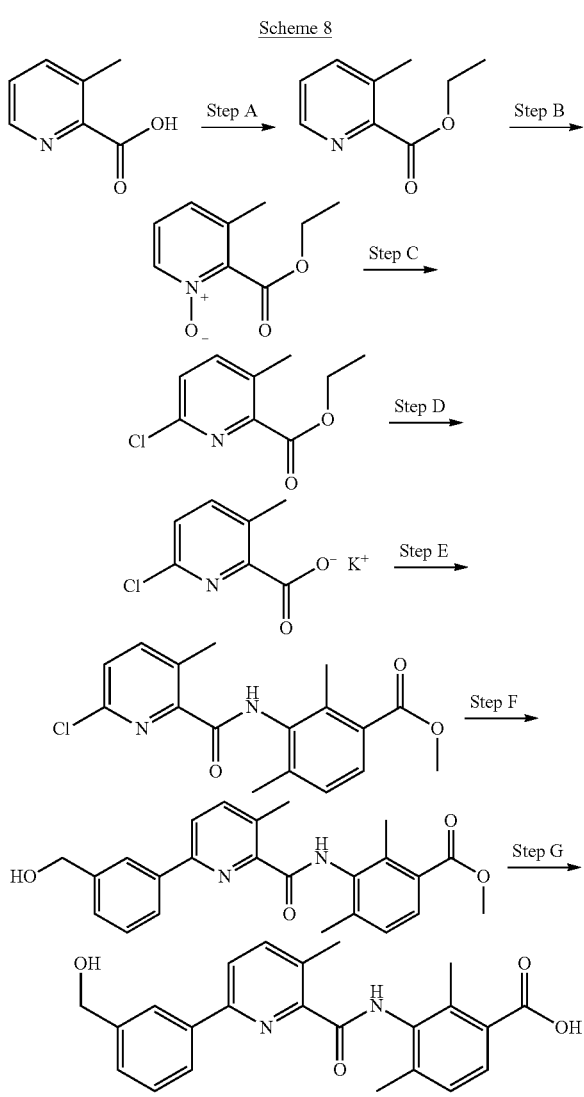

Scheme 8

Alternative synthesis of 3-[[6-[3-(hydroxymethyl)phenyl]-3-methyl-pyridine-2-carbonyl]amino]-2A-dimethyl-benzoic acid (Example 22)

Scheme 8, Step A.

Concentrated sulfuric acid (1.216 L, 21.9 mol) is added over 45 minutes to a solution of 3-methylpyridine-2-carboxylic acid (1000 g, 7.3 mol) in ethanol (10 L). The reaction is heated at reflux for 19 hours, cooled, and treated with solid sodium bicarbonate (~4 kg) to attain pH-8. The mixture is diluted with EtOAc (10 L) and filtered through filter cel. The solvent is removed under reduced pressure to give ethyl 3-methylpyridine-2-carboxylate (939 g, 78%). MS (m/z) 166 [M+H]+.

Scheme 8, Step B.

30% Hydrogen peroxide (1.52 L, 13.7 mol) is added to a solution of ethyl 3-methylpyridine-2-carboxylate (452 g, 2.74 mol) in HOAc (4.5 L). The mixture is heated at 60° C. for 4.5 hours, then cooled to room temperature overnight. The reaction is poured into sodium sulfite/ice water (10 L) and extracted with methylene chloride (2×4 L). The combined organic layers are dried over sodium sulfate and concentrated under reduced pressure to give ethyl 3-methyl-1-oxido-pyridin-1-ium-2-carboxylate as a pale yellow oil (502 g, quantitative). MS (m/z) 182 [M+H]+.

Scheme 8, Step C.

Phosphorous oxychloride (1.16 L, 12.4 mol) is added dropwise at 0° C. over ~1 hour to a solution of DMF (2.45 L, 24.8 mol) and methylene chloride (4.5 L) The reaction is stirred for 30 minutes at 0° C., then ethyl 3-methyl-1-oxido-pyridin-1-ium-2-carboxylate (450 g, 2.48 mol) is added. The reaction is allowed to slowly warm overnight to room temperature, and the reaction mixture is poured into ice water (10 L). The pH is adjusted with 10% sodium carbonate to pH-8, and the mixture is stirred for 1 hour. The layers are separated, and the aqueous layer is extracted with methylene chloride (2×2 L). The combined organic layers are dried over sodium sulfate, filtered, and concentrated under reduced pressure to give ethyl 6-chloro-3-methyl-pyridine-2-carboxylate as a beige semi solid (425 g, 86%). MS (m/z) 200 [M+H]+.

Scheme 8, Step D.

Ethyl 6-chloro-3-methyl-pyridine-2-carboxylate (750 g, 4.05 mol) is added in portions over ~20 minutes to a solution of KOH (272 g, 4.84 mol) in isopropanol (14 L). The mixture is stirred for 2 hours, filtered, and washed sequentially with isopropanol (500 mL) and heptanes (2 L). The solids are dried in vacuum at 50° C. for 48 hours to give potassium 6-chloro-3-methyl-pyridine-2-carboxylate as a white solid (767 g, 97%). MS (m/z) 210 [M+H]+.

Scheme 8, Step E.

Solid BOP-Cl (662.9 g, 2.604 mol) is added to a mixture of potassium 6-chloro-3-methyl-pyridine-2-carboxylate (300 g, 1.431 mol) in DMF (4.75 L). After a mild exotherm of ~5° C., the mixture is stirred for 1 hour. Methyl 3-amino-2,4-dimethyl-benzoate hydrochloride (277.7 g, 1.288 mol) and diisopropylethylamine (950 mL, 5.438 mol) are added sequentially to the reaction. The mixture is stirred overnight and poured into water (10 L) and ice (4 Kg). After stirring for 1 hour, the mixture is filtered, and the solid washed with water and dried in vacuum at 50° C. for 12 hours. The solids are slurried in heptanes (12 L) for 1 hour, filtered, and dried in vacuum at 50° C. to give methyl 3-[(6-chloro-3-methyl-pyridine-2-carbonyl)amino]-2,4-dimethyl-benzoate (430 g, 90%). MS (m/z) 333 [M+H]+.

Scheme 8, Step F.

2 M $Na_2CO_3$ (1.13 L, 2.253 mol) is added to a solution of methyl 3-[(6-chloro-3-methyl-pyridine-2-carbonyl)amino]-2,4-dimethyl-benzoate (250 g, 0.751 mol) and 3-(hydroxymethyl)phenyl boronic acid (137 g, 0.902 mol) in dioxane (2.5 L). The mixture is warmed to 40° C. and degassed with a stream of nitrogen for 1 hour. Palladium bistriphenylphosphine dichloride (26.4 g, 0.0376 mol) is added, and the reaction is degassed with a stream of nitrogen for an additional 20 minutes. The reaction is heated at reflux for 1.5 hours, cooled to room temperature, filtered through diatomaceous earth, and concentrated under reduced pressure to remove the organic solvent. The aqueous mixture is extracted with EtOAc (2×2 L). The combined organic layers are extracted with saturated brine, dried over sodium sulfate, filtered, and concentrated. This residue is dissolved in toluene (1.5 L) and loaded onto silica gel (2 kg). The column is eluted with a gradient of 0 to 50% EtOAc in heptanes. The product fractions are concentrated to a beige solid (~300 g). The solid is dissolved in 2-methyltetrahydrofuran (2.5 L), treated with mercaptopropyl silica gel, heated at 50° C. with stirring for 2 hours, and cooled overnight to room temperature. The mixture is filtered, and the silica gel is rinsed with EtOAc (3 L). The solvent is removed under reduced pressure to give white solid (297 g) that is diluted with isopropanol (1.5 L) and heated at reflux until a clear solution is obtained. The solution is cooled overnight, and the precipitate is isolated by filtration and dried in a vacuum oven at 50° C. to give methyl 3-[[6-[3-(hydroxymethyl)phenyl]-3-methyl-pyridine-2-carbonyl]amino]-2,4-dimethyl-benzoate (256 g, 84%). MS (m/z) 405[M+H]+.

Scheme 8, Step G.

Potassium hydroxide (86 g, 1.537 mol, 3 equiv) is added to a solution of methyl 3-[[6-[3-(hydroxymethyl)phenyl]-3-methyl-pyridine-2-carbonyl]amino]-2,4-dimethyl-benzoate (207 g, 0.512 mol) in MeOH (2 L). The reaction is heated at reflux for 16 hours, cooled to room temperature, and concentrated to dryness under reduced pressure. The residue is partitioned between water (2 L) and TBME. The aqueous layer is adjusted to pH-2 with 10% HCl, and the precipitate is filtered, washed with water (1 L) and heptanes (1 L) and dried in vacuum at 50° C. (197 g, 98%). The solids are combined with material from another run (226 g total) and refluxed in ethanol (2 L) for 2 hours. After cooling to room temperature, the solids are filtered and dried in a vacuum at 50° C. for 16 hours to give the title compound (211 g). MS (m/z) 391[M+H]+.

EXAMPLE 25

4-[[6-(1,3-Benzodioxol-5-yl)-3-methyl-pyridine-2-carbonyl]amino]-3,5-dimethyl-benzoic acid

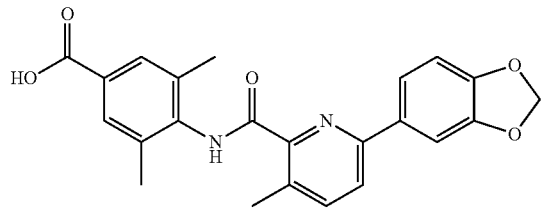 [SMILES: Cc1ccc(-c2ccc3c(c2)OCO3)nc1C(=O)Nc1c(C)cc(C(=O)O)cc1C]

Scheme 4, Step C.

To a solution of aqueous LiOH (50 mg, 1.18 mmol) in water (1.0 ml) is added methyl 4-[[6-(1,3-benzodioxol-5-yl)-3-methyl-pyridine-2-carbonyl]amino]-3,5-dimethyl-benzoate (240.0 mg, 0.573 mmol) in THF (2.0 ml) and MeOH (2.0 ml). After 3 hours at ambient temperature, the reaction mixture is acidified to pH 1-2 with aqueous 1N HCl solution and extracted with EtOAc. The combined organic layers are dried over sodium sulfate, filtered, and concentrated under reduced pressure. The residue is crystallized from diethyl ether to give the title compound (0.2 g, 86.4%). MS (m/z): 405.2 (M+1)+.

Scheme 9

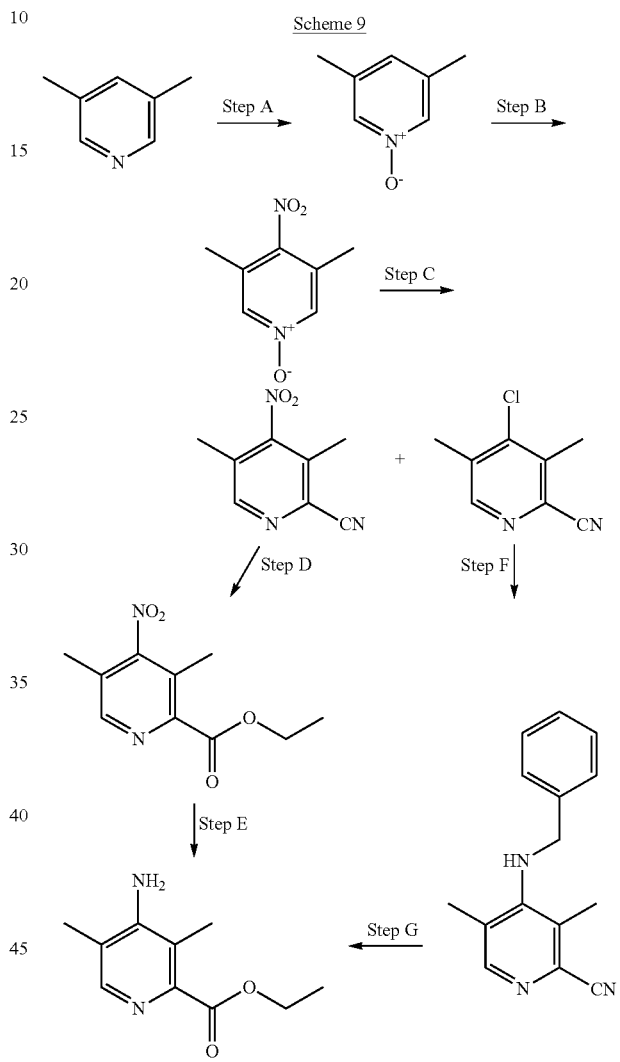

Preparation 39

Ethyl 4-amino-3,5-dimethyl-pyridine-2-carboxylate

Scheme 9, Step A.

To a solution of 3,5-dimethylpyridine (20.0 g, 186.65 mmol) in acetic acid (8 ml) at room temperature is added hydrogen peroxide (60.0 ml, 1.96 mol). After heating at 70° C. for 24 hours, the reaction mixture is diluted with water and extracted with 5% MeOH:$CH_2Cl_2$. The organic layers are combined and dried over anhydrous $Na_2SO_4$, filtered, and concentrated under reduced pressure. The residue is purified by silica gel chromatography using 10% MeOH in $CH_2Cl_2$ to give 3,5-dimethyl-1-oxido-pyridin-1-ium as off white powder (12.2 g, 53.1%). Mass spectrum (m/z): 124.1 (M+1)+.

Scheme 9, Step B.

To nitric acid (20.0 ml, 463.08 mmol) is slowly added sulfuric acid (60 ml, 1.13 mol) at 0° C., followed by 3,5-dimethyl-1-oxido-pyridin-1-ium (8.0 g, 64.96 mmol). The reaction mixture is heated to 70° C. for 6 hours, diluted with water, and extracted with 5% MeOH:CH$_2$Cl$_2$. The organic layers are combined and dried over anhydrous Na$_2$SO$_4$, filtered, and concentrated under reduced pressure. The residue is purified by silica gel chromatography using 10% MeOH in CH$_2$Cl$_2$ to give 3,5-dimethyl-4-nitro-1-oxido-pyridin-1-ium (3.8 g, 34.8%). Mass spectrum (m/z): 169.09 (M+1)$^+$.

Scheme 9, Step C.

To a solution of 3,5-dimethyl-4-nitro-1-oxido-pyridin-1-ium (3.5 g, 20.69 mmol) and zinc cyanide (4.86 g, 41.38 mmol) in acetonitrile (30 ml) is added dropwise under argon N,N-dimethylcarbamoyl chloride (2.86 ml, 31.04 mmol). After heating at 100° C. for 16 hours, the reaction mixture is diluted with ice-water and extracted with EtOAc. The organic layers are combined and dried over anhydrous Na$_2$SO$_4$, filtered, and concentrated under reduced pressure. The residue is purified by silica gel chromatography using 20% EtOAc/in Hexanes to give two compounds: 3,5-dimethyl-4-nitro-pyridine-2-carbonitrile (0.47 g, 12.8%). $^1$H NMR (300.16 MHz, CDCl3): δ 8.58 (s, 1H), 2.52 (s, 3H), 2.39 (s, 3H) and 4-chloro-3,5-dimethyl-pyridine-2-carbonitrile (1.05 g, 30.5%). Mass spectrum (m/z): 167.07 (M+1)$^+$.

Scheme 9, Step D.

To a solution of 3,5-dimethyl-4-nitro-pyridine-2-carbonitrile (0.45 g, 2.54 mmol) in ethanol (2 ml) is added dropwise concentrated sulfuric acid (2 ml, 37.52 mmol) at 0° C. After heating at 90° C. for 18 hours, the reaction mixture is poured onto ice and extracted with EtOAc. The organic layers are combined and dried over anhydrous Na$_2$SO$_4$, filtered, and concentrated under reduced pressure. The residue is purified by silica gel flash chromatography using 40% EtOAc in Hexanes to give ethyl 3,5-dimethyl-4-nitro-pyridine-2-carboxylate (0.35 g, 61.5%). Mass spectrum (m/z): 225.1 (M+1)$^+$.

Scheme 9, Step E.

To a solution of ethyl 3,5-dimethyl-4-nitro-pyridine-2-carboxylate (0.30 g, 1.34 mmol), in ethanol (5 ml) is added 10% Pd on activated carbon (0.06 g), and the mixture is purged with argon for 10 min, followed by the addition of hydrogen gas. After 5 hours, the reaction mixture is filtered through diatomaceous earth and washed with ethanol. The filtrate is concentrated under reduced pressure to give ethyl 4-amino-3,5-dimethyl-pyridine-2-carboxylate (0.24 g, 92.3%). Mass spectrum (m/z): 195.17 (M+1)$^+$.

Scheme 9, Step F.

To a solution of 4-chloro-3,5-dimethyl-pyridine-2-carbonitrile (0.6 g, 3.60 mmol) and phenylmethylamine (0.58 g, 5.40 mmol) in 1,4-dioxane (6 ml) purged with argon is added cesium carbonate (3.52 g, 10.8 mmol), S-Phos (147.5 mg, 0.36 mmol), and Tris(dibenzylideneacetone)dipalladium(0) (329.7 mg, 0.60 mmol). After heating at 100° C. for 4 hours, the reaction mixture is filtered through filter cel and washed with EtOAc. The filtrate is concentrated under reduced pressure, and the residue is purified by silica gel chromatography using 40% EtOAc in Hexanes to give 4-(benzylamino)-3,5-dimethyl-pyridine-2-carbonitrile (0.61 g, 71.4%). Mass spectrum (m/z): 238.06 (M+1)$^+$.

Scheme 9, Step G.

To a solution of 4-(benzylamino)-3,5-dimethyl-pyridine-2-carbonitrile (0.6 g, 2.53 mmol) in ethanol (5.0 ml) at 0° C. is added dropwise concentrated sulfuric acid (5.0 ml), and the reaction mixture is warmed to room temperature. After heating at 100° C. for 32 hours, the reaction mixture is diluted with saturated solution of NaHCO$_3$ and extracted with EtOAc. The combined organic layers are dried over anhydrous Na$_2$SO$_4$, filtered, and concentrated under reduced pressure. The residue is purified by silica gel flash chromatography using 10% MeOH in CH$_2$Cl$_2$ to give the title compound (0.4 g, 81.4%). Mass spectrum (m/z): 195.1 (M+1)$^+$.

Scheme 10

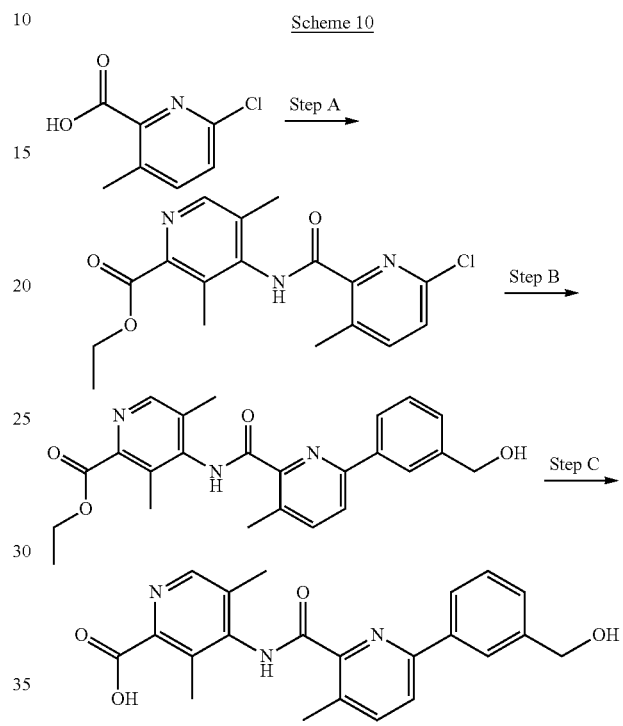

EXAMPLE 26

4-[[6-[3-(Hydroxymethyl)phenyl]-3-methyl-pyridine-2-carbonyl]amino]-3,5-dimethyl-pyridine-2-carboxylic acid Scheme 10, Step A.

To a solution of 6-chloro-3-methyl-pyridine-2-carboxylic acid (220 mg, 1.28 mmol) in THF (15 mL) under argon at 0° C. are added isobutyl chloroformate (192.6 mg, 1.41 mmol) and N-methylmorpholine (259.4 mg, 2.56 mmol). The reaction mixture is stirred at 0° C. for 40 min, and a solution of ethyl 4-amino-3,5-dimethyl-pyridine-2-carboxylate (249 mg, 1.28 mmol) in THF (1.5 ml) is added. After 18 hours at 50° C., the reaction mixture is poured onto a column packed with neutral alumina and purified by flash chromatography eluting with 40% EtOAc in Hexanes to give ethyl 4-[(6-chloro-3-methyl-pyridine-2-carbonyl)amino]-3,5-dimethyl-pyridine-2-carboxylate (0.03 g, 7.6%). Mass spectrum (m/z): 348.0 (M+1)$^+$.

Scheme 10, Step B.

To a solution of ethyl 4-[(6-chloro-3-methyl-pyridine-2-carbonyl)amino]-3,5-dimethyl-pyridine-2-carboxylate (30 mg, 0.09 mmol) in 1,4-dioxane (1.0 mL) and water (0.5 ml) is added (3-(hydroxymethyl)phenyl)boronic acid (14.4 mg, 0.09 mmol) followed by Cs$_2$CO$_3$ (56.2 mg, 0.172 mmol) and PdCl$_2$(dppf).CH$_2$Cl$_2$ (14.1 mg, 0.017 mmol). The reaction mixture is purged with argon for 5 minutes and then heated at 100° C. After 2 hours, the reaction mixture is cooled to room temperature, filtered through diatomaceous earth, and washed with EtOAc. The filtrate is concentrated, and the residue is purified by silica gel flash chromatography using 50% EtOAc in hexane to afford ethyl 4-[[6-[3-(hydroxymethyl)phenyl]-3-methyl-pyridine-2-carbonyl]amino]-3,5-dimethyl-pyridine-2-carboxylate as a colorless oil (0.02 g, 60.8%). Mass spectrum (m/z): 420.3 (M+1)$^+$.

Scheme 10, Step C.

To a solution of aqueous LiOH (18.01 mg, 0.429 mmol) in water (1 ml) is added ethyl 4-[[6-[3-(hydroxymethyl)phenyl]-3-methyl-pyridine-2-carbonyl]amino]-3,5-dimethyl-pyridine-2-carboxylate (36 mg, 0.09 mmol) in THF (1 ml) and MeOH (1 ml). After 3 hours at ambient temperature, the reaction mixture is acidified to pH 1-2 with aqueous 1N HCl solution and extracted with EtOAc. The combined organic layers are dried over sodium sulfate, filtered, and concentrated under reduced pressure. The residue is triturated with pentane and filtered to give the title compound (0.02 g, 56.8%). Mass spectrum (m/z): 392.2 (M+1)$^+$.

Preparation 40

Methyl 5-amino-4,6-dimethyl-pyridine-2-carboxylate

Scheme 11, Step A.

To a solution of 3-amino-2,4-dimethylpyridine (1 g, 8.19 mmol) in methylene chloride (40.0 ml) is added a solution of bromine (0.55 ml, 40.64 mmol) in methylene chloride (10.0 ml) at 0° C. over 5 min. After 12 hours at ambient temperature, the reaction mixture is diluted with water and extracted with EtOAc. The combined organic layers are dried over sodium sulfate, filtered, and concentrated under reduced pressure. The residue is purified by silica gel chromatography using 10-100% EtOAc in hexanes to afford 6-bromo-2,4-dimethyl-pyridin-3-amine (992 mg, 60.3%). Mass spectrum (m/z): 201.0 (M+1)$^+$.

Scheme 11, Step B.

To a 100 ml Parr autoclave with mechanical stirring is added 6-bromo-2,4-dimethyl-pyridin-3-amine (0.99 g, 4.92 mmol), Pd(OAc)$_2$ (112 mg, 0.50 mmol), PdCl$_2$(dppf).CH$_2$Cl$_2$ (331 mg, 0.6 mmol), CH$_3$CN (30.0 ml), triethylamine (1.75 ml), and MeOH (20.0 ml). The Parr autoclave is sealed, purged, and pressurized with CO to 689.5 kPa (100 psig). The mixture is heated at 85° C. for 3 hours. The mixture is cooled to ambient temperature and vented. The mixture is filtered, rinsed with MeOH, and concentrated to dryness under reduced pressure. The residue is purified by silica gel flash chromatography using a gradient of 0-5% 2M NH$_3$/MeOH in methylene chloride as eluent. The product fractions are combined and concentrated. The residue is triturated with EtOAc and filtered. The filtrate is concentrated to give the title compound (537.0 mg, 60.4%). Mass spectrum (m/z): 181.0 (M+1)$^+$.

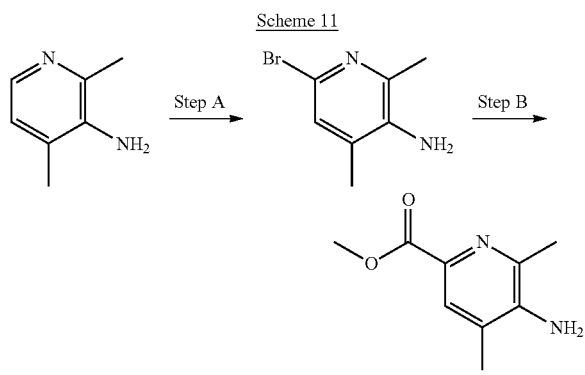

Scheme 11

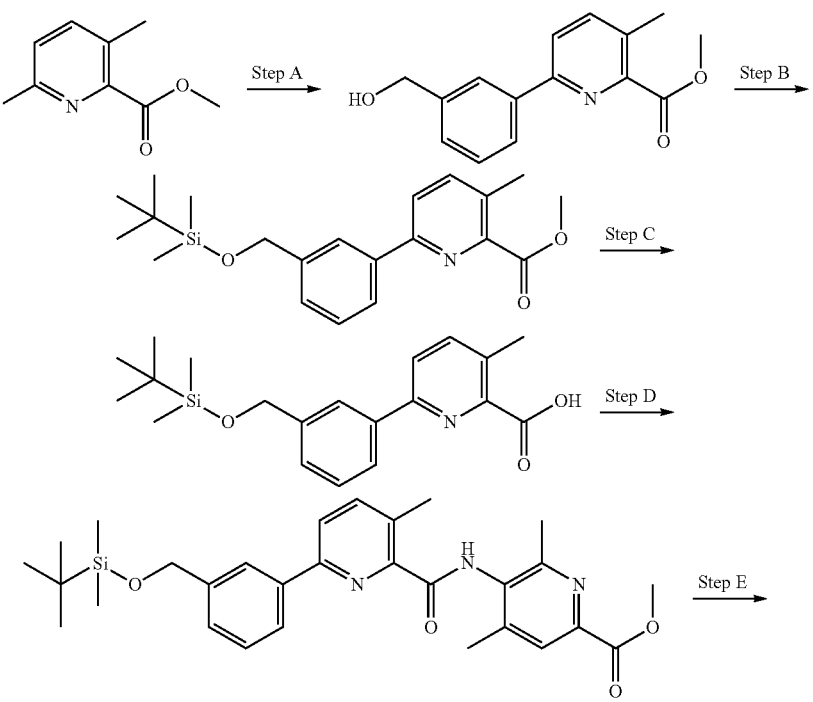

Scheme 12

-continued

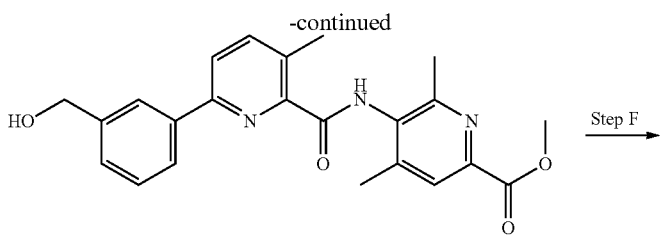

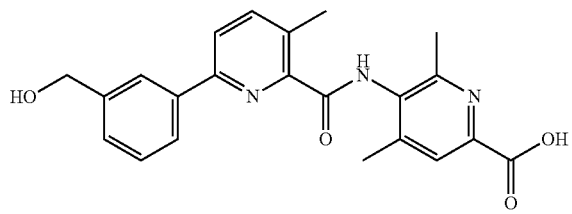

EXAMPLE 27

5-[[6-[3-(Hydroxymethyl)phenyl]-3-methyl-pyridine-2-carbonyl]amino]-4,6-dimethyl-pyridine-2-carboxylic acid Scheme 12, Step A.

To a solution of methyl 6-chloro-3-methyl-pyridine-2-carboxylate (1.0 g, 5.39 mmol) in 1,4-dioxane (17.9 ml) and H$_2$O (2.9 ml) is added (3-(hydroxymethyl)phenyl)boronic acid (0.982 g, 6.47 mmol) followed by K$_2$CO$_3$ (1.86 g, 13.47 mmol) and PdCl$_2$(dppf).CH$_2$Cl$_2$ (131.9 mg, 0.13 mmol). The reaction mixture is purged with argon for 5 minutes and then heated at 110° C. After 2 hours, the reaction is cooled to room temperature, diluted with water and extracted with EtOAc. The combined organic layers are dried over magnesium sulfate, filtered, and concentrated. The residue is purified by silica gel flash chromatography using 70% EtOAc in hexane to afford methyl 6-[3-(hydroxymethyl)phenyl]-3-methyl-pyridine-2-carboxylate (0.713 g, 51.4%). Mass spectrum (m/z): 258.0 (M+1)$^+$.

Scheme 12, Step B.

To a solution of methyl 6-[3-(hydroxymethyl)phenyl]-3-methyl-pyridine-2-carboxylate (713.0 mg, 2.77 mmoles) in CH$_2$Cl$_2$ (13.9 ml) is added 1H-imidazole (285.8 mg, 4.16 mmoles) followed by t-butyldimethylchlorosilane (516.7 mg, 3.33 mmoles). The reaction mixture is stirred at room temperature for 2 hours and then washed sequentially with water, saturated NaHCO$_3$ solution, and brine. The combined organic layers are dried over magnesium sulfate, filtered, and concentrated to afford methyl 6-[3-[[tert-butyl(dimethyl)silyl]oxymethyl]phenyl]-3-methyl-pyridine-2-carboxylate (920.0 mg, 89.4%). Mass spectrum (m/z): 372.2 (M+1)$^+$.

Scheme 12, Step C.

A solution of aqueous 1N LiOH (207.8 mg, 4.95 mmol) is added to a stirred solution of methyl 6-[3-[[tert-butyl(dimethyl)silyl]oxymethyl]phenyl]-3-methyl-pyridine-2-carboxylate (920.0 mg, 2.48 mmol) in THF (5.0 ml) and MeOH (5.0 mL). After stirring at ambient temperature for 2 hours, the mixture is diluted with water and extracted with 10% MeOH/methylene chloride. The combined organic layers are dried over magnesium sulfate, filtered and concentrated. The residue is purified by silica gel flash chromatography using 0-100% EtOAc in hexanes to give 6-[3-[[tert-Butyl(dimethyl)silyl]oxymethyl]phenyl]-3-methyl-pyridine-2-carboxylic acid (589.0 mg, 66.5%). Mass spectrum (m/z): 358.2 (M+1)$^+$.

Scheme 12, Step D.

To a solution of 6-[3-[[tert-butyl(dimethyl)silyl]oxymethyl]phenyl]-3-methyl-pyridine-2-carboxylic acid (300.0 mg, 0.839 mmol) in THF (8.4 ml) at 0° C. is added isobutyl chloroformate (128.6 mg, 0.923 mmol) and N-methylmorpholine (101.8 mg, 1.01 mmol). The reaction mixture is stirred at 0° C. for 20 minutes, and a solution of methyl 5-amino-4,6-dimethyl-pyridine-2-carboxylate (151.2 mg, 0.839 mmol) in THF (2.0 ml) is added. The reaction mixture is warmed up to ambient temperature. After 12 hours, the reaction mixture is diluted with water and extracted with EtOAc. The combined organic layers are dried over sodium sulfate, filtered, and concentrated. The residue is purified by silica gel flash chromatography using 0-40% EtOAc in hexanes to give methyl 5-[[6-[3-[[tert-butyl(dimethyl)silyl]oxymethyl]phenyl]-3-methyl-pyridine-2-carbonyl]amino]-4,6-dimethyl-pyridine-2-carboxylate (192 mg, 44%). Mass spectrum (m/z): 520.2 (M+1)$^+$.

Scheme 12, Step E.

To a solution of methyl 5-[[6-[3-[[tert-butyl(dimethyl)silyl]oxymethyl]phenyl]-3-methyl-pyridine-2-carbonyl]amino]-4,6-dimethyl-pyridine-2-carboxylate (190 mg, 0.366 mmol) in THF (2.0 ml) is added Bu$_4$NF 1.0 M in THF (0.548 ml, 0.548 mmol) at 0° C. The reaction mixture is gradually warmed to ambient temperature. After 2 hours, the reaction mixture is diluted with ice-water and extracted with EtOAc. The combined organic layers are dried over sodium sulfate, filtered, and concentrated. The residue is purified by silica gel flash chromatography using 0-40% EtOAc in hexane to afford methyl 5-[[6-[3-(hydroxymethyl)phenyl]-3-methyl-pyridine-2-carbonyl]amino]-4,6-dimethyl-pyridine-2-carboxylate (133.0 mg, 89.8%). Mass spectrum (m/z): 406.2 (M+1)$^+$.

Scheme 12, Step F.

A solution of aqueous 1N NaOH (0.64 ml) is added to a stirred solution of methyl 5-[[6-[3-(hydroxymethyl)phenyl]-3-methyl-pyridine-2-carbonyl]amino]-4,6-dimethyl-pyridine-2-carboxylate (130.0 mg, 0.32 mmol) in THF (2.0 ml) and MeOH (2.0 ml). After 2 hours at ambient temperature, the reaction mixture is acidified to pH 1-2 with aqueous 1N HCl solution. The resulting precipitate is filtered, washed with water, and dried at 40° C. in vacuum oven for 1 hour to give the title compound as a white solid (88.0 mg, 70.0%). Mass spectrum (m/z): 392.2 (M+1)$^+$.

Scheme 13

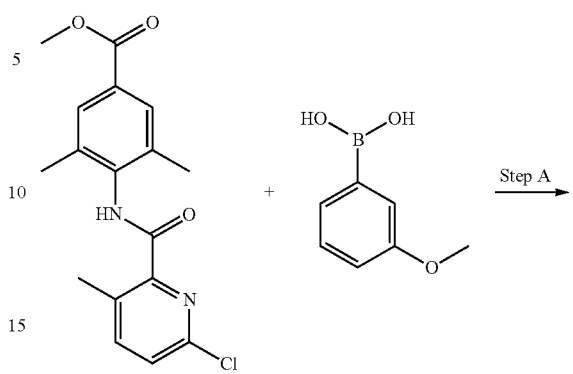

Preparation 41

Methyl 4-[[6-chloro-3-(trifluoromethyl)pyridine-2-carbonyl]amino]-3,5-dimethyl-benzoate

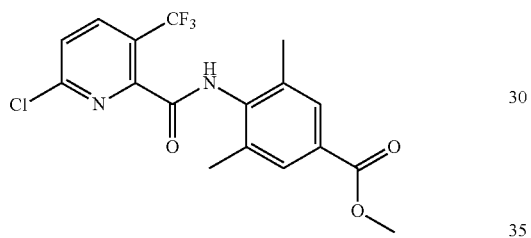

To a solution of 6-chloro-3-(trifluoromethyl)pyridine-2-carboxylic acid (0.40 g, 1.77 mmol) in CH$_2$Cl$_2$ (8.0 ml) at room temperature are added methyl 4-amino-3,5-dimethyl-benzoate (0.318 mg, 1.77 mmol) and diisopropylethylamine (0.573 g, 4.43 mmol). After stirring the mixture for 10 minutes, 1-propanephosphonic acid cyclic anhydride (50% solution in EtOAc, 1.35 g, 2.13 mmol) is added via syringe. After 36 hours at ambient temperature, the reaction mixture is heated at 50° C. for 7 days. The reaction mixture is concentrated and triturated with MeOH to give the title compound as white solid (456.0 mg, 66.5%). Mass spectrum (m/z): 387.2 (M+1).

The following compound is prepared essentially by the method described above in preparation 41, using the appropriate carboxylic acid and amine:

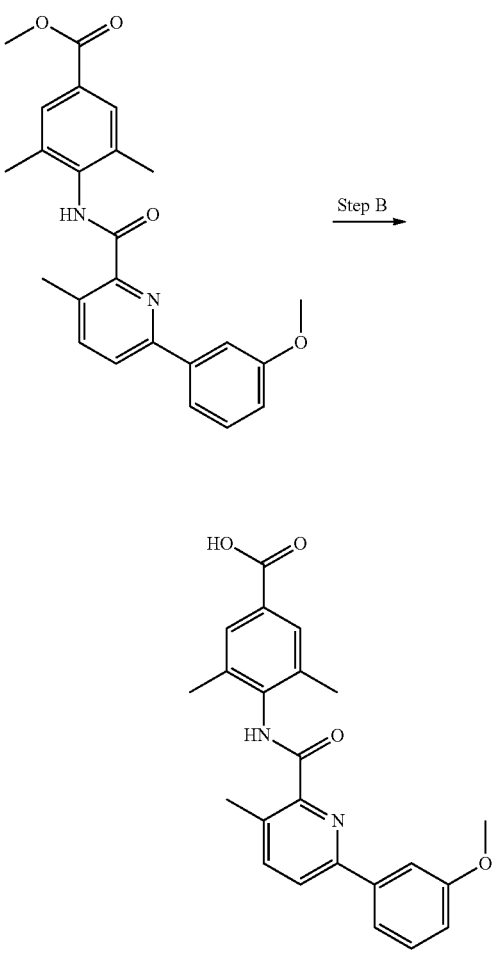

| Prep. | Chemical Name | Structure | MS (m/z) |
|---|---|---|---|
| 42 | Methyl 3-[[6-chloro-3-(trifluoromethyl)pyridine-2-carbonyl]amino]-2,4-dimethyl-benzoate | 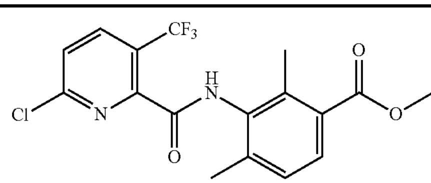 | 387.0 (M + H)$^+$ |

Preparation 43

Methyl 4-[[6-(3-methoxyphenyl)-3-methyl-pyridine-2-carbonyl]amino]-3,5-dimethyl-benzoate

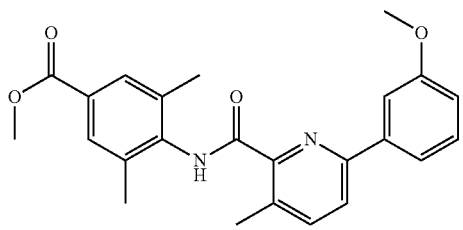 [SMILES: COC(=O)c1cc(C)c(NC(=O)c2nc(-c3cccc(OC)c3)ccc2C)c(C)c1]

Scheme 13, Step A.

A mixture of methyl 4-[(6-chloro-3-methyl-pyridine-2-carbonyl)amino]-3,5-dimethyl-benzoate (200 mg, 1.18 mmol), (3-methoxyphenyl)boronic acid (198 mg, 1.3 mmol), potassium carbonate (170 mg, 1.23 mmol), and), $PdCl_2(dppf).CH_2Cl_2$ (20 mg) in dioxane (4 mL) and water (1 mL) is heated to 110° C. in a microwave reactor for 120 minutes. The mixture is filtered through a hydrophobic frit and washed with methylene chloride (2×10 mL). The filtrate is concentrated and purified by silica gel chromatography using 15% ethyl acetate in hexane to provide methyl 4-[[6-(3-methoxyphenyl)-3-methyl-pyridine-2-carbonyl]amino]-3,5-dimethyl-benzoate as product (194 mg, 41% yield). Mass spectrum (m/z): 405.2 (M+H)⁺.

The following compounds are prepared essentially by the method described above in preparation 43, using the appropriate carboxylic ester and boronic acid:

| Prep | Chemical Name | Structure | MS (m/z) |
|---|---|---|---|
| 44 | Methyl 3-[[6-(3-fluorophenyl)-3-methyl-pyridine-2-carbonyl]amino]-2,4-dimethyl benzoate | 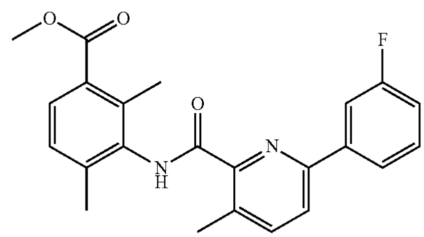 | 393.2 (M + H)⁺ |
| 45 | Methyl 2,4-dimethyl-3-[[3-methyl-6-[3-(trifluoromethyl)phenyl]pyridine-2-carbonyl]amino]benzoate | 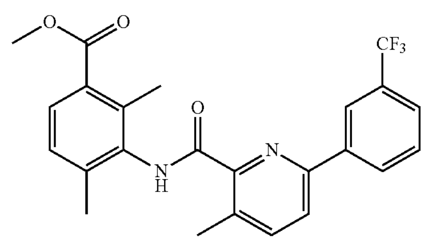 [SMILES: COC(=O)c1ccc(C)c(NC(=O)c2nc(-c3cccc(C(F)(F)F)c3)ccc2C)c1C] | 443.0 (M + H)⁺ |
| 46 | Methyl 2,4-dimethyl-3-[[3-methyl-6-(m-tolyl)pyridine-2-carbonyl]amino]benzoate | 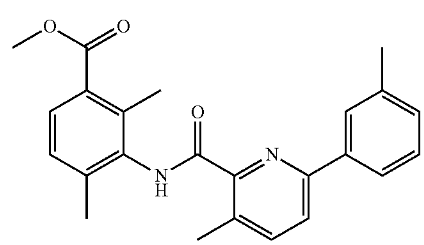 | 389.2 (M + H)⁺ |
| 47 | Methyl 2,4-dimethyl-3-[[3-methyl-6-[3-(trifluoromethoxy)phenyl]pyridine-2-carbonyl]amino]benzoate | 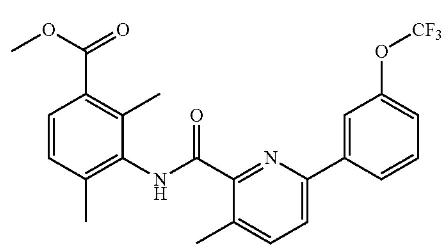 [SMILES: COC(=O)c1ccc(C)c(NC(=O)c2nc(-c3cccc(OC(F)(F)F)c3)ccc2C)c1C] | 459.0 (M + H)⁺ |

-continued

| Prep | Chemical Name | Structure | MS (m/z) |
|---|---|---|---|
| 48 | Methyl 3-[[6-(3-methoxyphenyl)-3-methyl-pyridine-2-carbonyl]amino]-2,4-dimethyl-benzoate | 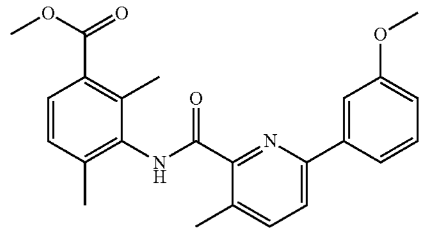 | 405.2 (M + H)+ |
| 49 | Methyl 3-[[6-(3-methoxyphenyl)-3-methyl-pyridine-2-carbonyl]amino]-2,4-dimethyl-benzoate | 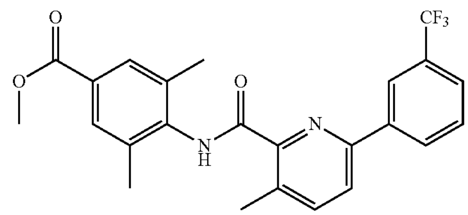 [SMILES: COC(=O)c1cc(C)c(NC(=O)c2nc(-c3cccc(C(F)(F)F)c3)ccc2C)c(C)c1] | 443.0 (M + H)+ |
| 50 | Methyl 3,5-dimethyl-4-[[3-methyl-6-[3-(trifluoromethoxy)phenyl]pyridine-2-carbonyl]amino]benzoate | 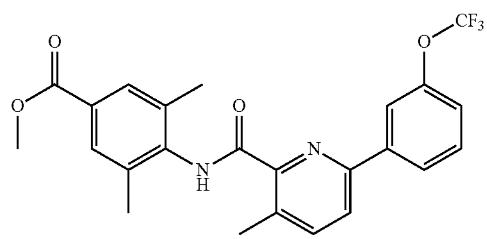 [SMILES: COC(=O)c1cc(C)c(NC(=O)c2nc(-c3cccc(OC(F)(F)F)c3)ccc2C)c(C)c1] | 459.0 (M + H)+ |

EXAMPLE 28

4-[[6-(3-Methoxyphenyl)-3-methyl-pyridine-2-carbonyl]amino]-3,5-dimethyl-benzoic acid Scheme 13, Step B.

A slurry of methyl 4-[[6-(3-methoxyphenyl)-3-methyl-pyridine-2-carbonyl]amino]-3,5-dimethyl-benzoate (194 mg, 0.479 mmol) in MeOH (3 mL), THF (2 mL), and 1N NaOH (1.2 mL) is stirred at RT over 3 nights. The reaction mixture is treated with 1N HCl (1.2 mL) and diluted with water. The solid is collected by vacuum filtration and dried under reduced pressure to provide the title compound (172 mg, 92% yield). Mass spectrum (m/z): 391.2 (M+H)+.

The following compounds are prepared essentially by the method described above in Example 28, using the appropriate carboxylic ester:

| Ex. | Chemical Name | Structure | MS (m/z) |
|---|---|---|---|
| 29 | 3-[[6-(3-Fluorophenyl)-3-methyl-pyridine-2-carbonyl]amino]-2,4-dimethyl benzoic acid | 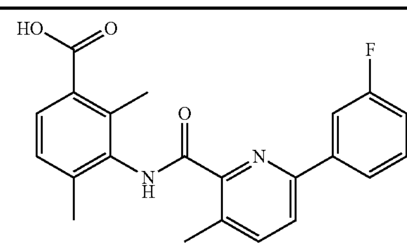 | 379.2 (M + H)+ |

-continued

| Ex. | Chemical Name | Structure | MS (m/z) |
|---|---|---|---|
| 30 | 2,4-Dimethyl-3-[[3-methyl-6-[3-(trifluoromethyl)phenyl]pyridine-2-carbonyl]amino]benzoic acid | 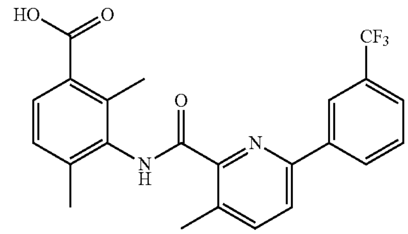 [SMILES: Cc1ccc(-c2cccc(C(F)(F)F)c2)nc1C(=O)Nc1c(C)ccc(C(=O)O)c1C] | 429.2 (M + H)+ |
| 31 | 2,4-Dimethyl-3-[[3-methyl-6-(m-tolyl)pyridine-2-carbonyl]amino]benzoic acid | 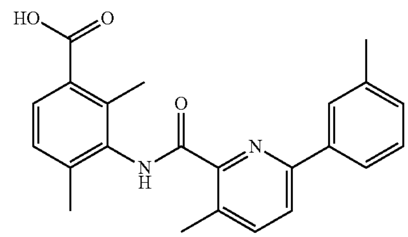 [SMILES: Cc1cccc(-c2ccc(C)c(C(=O)Nc3c(C)ccc(C(=O)O)c3C)n2)c1] | 375.2 (M + H)+ |
| 32 | 2,4-Dimethyl-3-[[3-methyl-6-[3-(trifluoromethoxy)phenyl]pyridine-2-carbonyl]amino]benzoic acid | 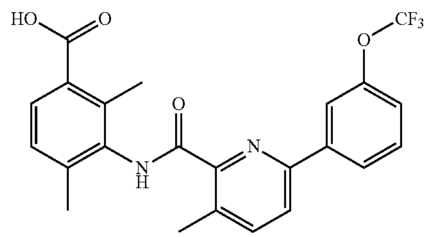 [SMILES: Cc1ccc(-c2cccc(OC(F)(F)F)c2)nc1C(=O)Nc1c(C)ccc(C(=O)O)c1C] | 445.2 (M + H)+ |
| 33 | 3-[[6-(3-Methoxyphenyl)-3-methyl-pyridine-2-carbonyl]amino]-2,4-dimethyl-benzoic acid | 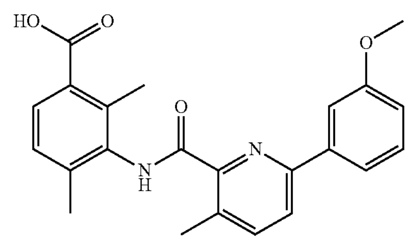 [SMILES: COc1cccc(-c2ccc(C)c(C(=O)Nc3c(C)ccc(C(=O)O)c3C)n2)c1] | 391.2 (M + H)+ |
| 34 | 3-[[6-(3-Methoxyphenyl)-3-methyl-pyridine-2-carbonyl]amino]-2,4-dimethyl-benzoate | 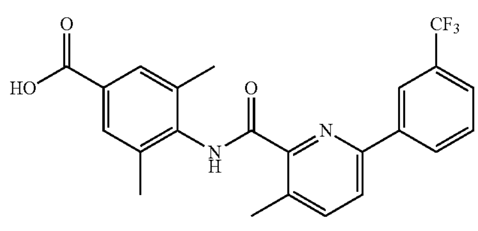 [SMILES: Cc1ccc(-c2cccc(C(F)(F)F)c2)nc1C(=O)Nc1c(C)cc(C(=O)O)cc1C] | 429.2 (M + H)+ |
| 35 | 3,5-Dimethyl-4-[[3-methyl-6-[3-(trifluoromethoxy)phenyl]pyridine-2-carbonyl]amino]benzoic acid | 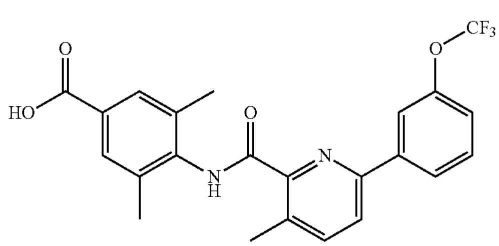 [SMILES: Cc1ccc(-c2cccc(OC(F)(F)F)c2)nc1C(=O)Nc1c(C)cc(C(=O)O)cc1C] | 445.2 (M + H)+ |

Scheme 14

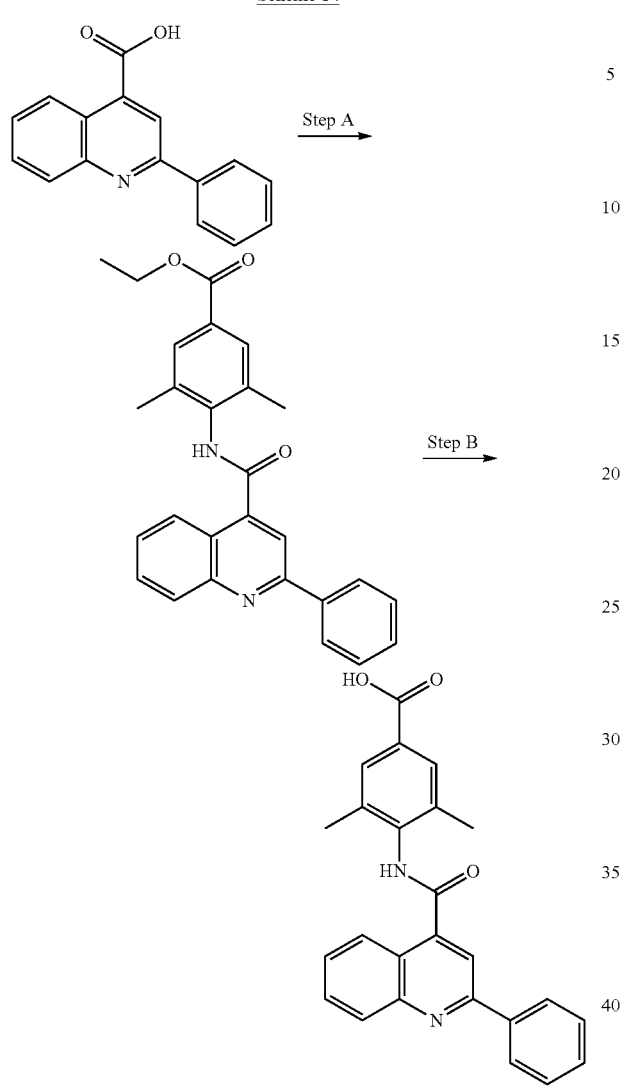

EXAMPLE 36

3,5-Dimethyl-4-[(2-phenylquinoline-4-carbonyl) amino]benzoic acid

Scheme 14, Step A.

To a solution of 2-phenylquinoline-4-carboxylic acid (193.5 g, 0.776 mmol) in $CH_2Cl_2$ (6.0 ml) at 0° C. are added ethyl 4-amino-3,5-dimethyl-benzoate (150.0 g, 0.776 mmol), and N,N-diisopropylethylamine (0.338 ml, 1.94 mmol). The reaction mixture is stirred for 10 minutes and 1-propanephosphonic acid cyclic anhydride (50% solution in ethyl acetate, 0.555 ml, 0.932 mmol) is added via syringe. The mixture is stirred at ambient temperature for 48 hours, diluted with water, and extracted with EtOAc. The combined organic layers are dried over magnesium sulfate, filtered, and concentrated under reduced pressure. The residue is triturated with $CH_2Cl_2$ and filtered to give ethyl 3,5-dimethyl-4-[(2-phenylquinoline-4-carbonyl)amino]benzoate as a white solid (93.5 mg, 28.4%). Mass spectrum (m/z): 425.2 $(M+H)^+$.

Scheme 14, Step B.

A solution of aqueous 1N NaOH (1.0 ml) is added to a stirred solution of ethyl 3,5-dimethyl-4-[(2-phenylquinoline-4-carbonyl)amino]benzoate (93.5 mg, 0.220 mmol) in THF (3.0 ml). After heating at 50° C. for 8 hours, the reaction mixture is acidified to pH 1-2 with aqueous 1N HCl solution. The resulting precipitate is filtered, washed with water, and dried at 40° C. in vacuum oven for 1 hour to give the title compound as a white solid (70.0 mg, 80.2%). Mass spectrum (m/z): 397.2 $(M+H)^+$.

Scheme 15

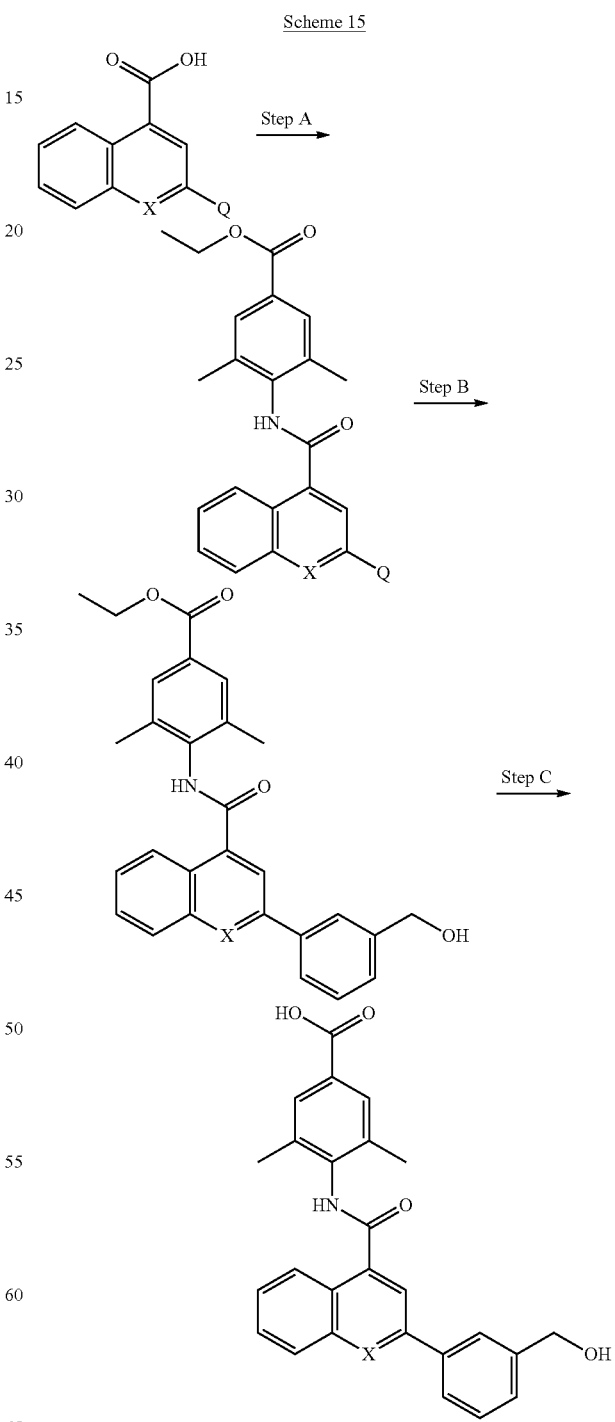

Q = Cl or Br

Preparation 51

Ethyl 4-[(2-chloroquinoline-4-carbonyl)amino]-3,5-dimethyl-benzoate

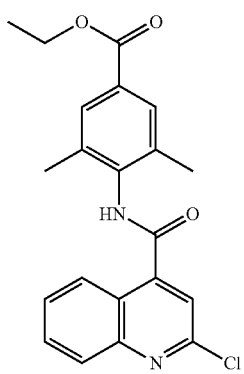 [SMILES: CCOC(=O)c1cc(C)c(NC(=O)c2cc(Cl)nc3ccccc23)c(C)c1]

Scheme 15, Step A.

To a solution of 2-chloroquinoline-4-carboxylic acid (1.07 g, 5.17 mmol) in $CH_2Cl_2$ (15 ml) at 0° C. are added ethyl 4-amino-3,5-dimethyl-benzoate (1.00 g, 5.17 mmol), and N,N-diisopropylethylamine (2.26 ml, 12.94 mmol). After stirring the reaction mixture for 10 minutes, 1-propanephosphonic acid cyclic anhydride (50% solution in ethyl acetate, 3.70 ml, 6.21 mmol) is added via syringe. The reaction mixture is stirred at ambient temperature for 24 hours, diluted with water, and extracted with EtOAc. The combined organic layers are dried over magnesium sulfate, filtered, and concentrated under reduced pressure. The resulting residue is triturated with MeOH and filtered. The filtrate is purified by high pH reverse phase chromatography (0-100% 10 mM ammonium bicarbonate in water with 5% MeOH/$CH_3CN$) to give the title compound as white solid (0.49 g, 25%). Mass spectrum (m/z): 383.1 (M+H)$^+$.

The following compounds are prepared essentially by the method described above in preparation 51, using the appropriate carboxylic acid and amine:

| Prep. | Chemical Name | Structure | MS (m/z) |
|---|---|---|---|
| 52 | Methyl 3-[(2-chloroquinoline-4-carbonyl)amino]-2,4-dimethyl-benzoate | 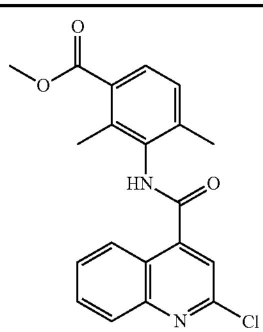 | 369.1 (M + H)$^+$ |
| 53 | Ethyl 4-[(3-bromonaphthalene-1-carbonyl)amino]-3,5-dimethyl-benzoate | | 426.0 (M + H)$^+$ |

Preparation 54

Ethyl 4-[[2-[3-(hydroxymethyl)phenyl]quinoline-4-carbonyl]amino]-3,5-dimethyl-benzoate

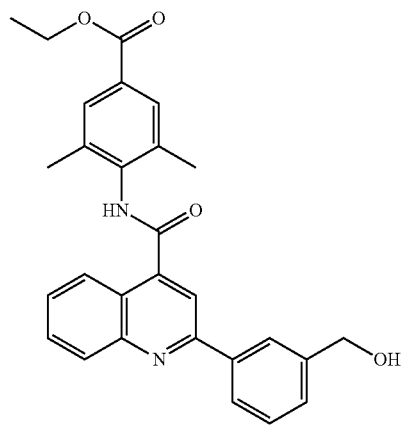 [SMILES: CCOC(=O)c1cc(C)c(NC(=O)c2cc(-c3cccc(CO)c3)nc3ccccc23)c(C)c1]

Scheme 15, Step B.

To a solution of ethyl 4-[(2-chloroquinoline-4-carbonyl)amino]-3,5-dimethyl-benzoate (0.49 g, 1.27 mmol) in 1,4-dioxane (17.0 ml) and $H_2O$ (2.5 ml) is added (3-(hydroxymethyl)phenyl)boronic acid (231.9 mg, 1.53 mmol) followed by $K_2CO_3$ (439.2 mg, 3.18 mmol) and $PdCl_2(dppf) \cdot CH_2Cl_2$ (103.9 mg, 0.0127 mmol). The reaction mixture is purged with argon for 5 minutes and then heated at 110° C. After 3 hours, the mixture is cooled, diluted with water, and extracted with ethyl acetate. The combined organic layers are dried over sodium sulfate, filtered, and concentrated. The residue is purified by silica gel flash chromatography using 40% ethyl acetate in hexane to afford the title compound (0.42 g, 72.3%). Mass spectrum (m/z): 455.2 (M+H)$^+$.

The following compounds are prepared essentially by the method described above in preparation 54, using the appropriate carboxylic ester and boronic acid:

| Prep. | Chemical Name | Structure | MS (m/z) |
|---|---|---|---|
| 55 | Methyl 3-[[2-[3-(hydroxymethyl)phenyl]quinoline-4-carbonyl]amino]-2,4-dimethyl-benzoate | 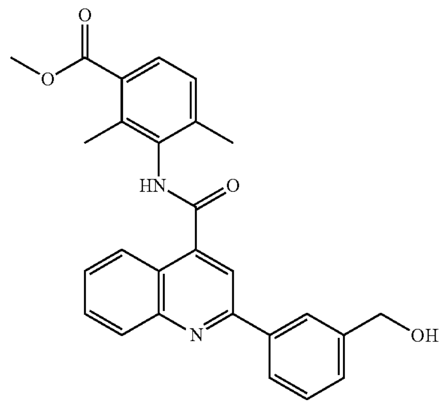 [SMILES: COC(=O)c1ccc(C)c(NC(=O)c2cc(-c3cccc(CO)c3)nc3ccccc23)c1C] | 441.2 (M + H)+ |
| 56 | Ethyl 3,5-dimethyl-4-[(3-phenylnaphthalene-1-carbonyl)amino]benzoate | 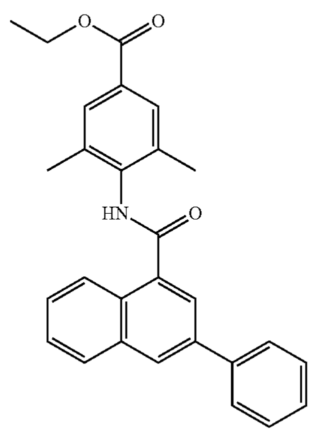 [SMILES: CCOC(=O)c1cc(C)c(NC(=O)c2cc(-c3ccccc3)cc3ccccc23)c(C)c1] | 424.0 (M + H)+ |
| 57 | Ethyl 4-[[3-[3-(hydroxymethyl)phenyl]naphthalene-1-carbonyl]amino]-3,5-dimethyl-benzoate | 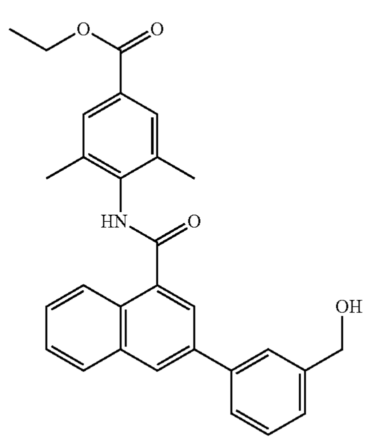 [SMILES: CCOC(=O)c1cc(C)c(NC(=O)c2cc(-c3cccc(CO)c3)cc3ccccc23)c(C)c1] | a) |

| Prep. | Chemical Name | Structure | MS (m/z) |
|---|---|---|---|
| 58 | Methyl 2,4-dimethyl-3-[(3-phenylnaphthalene-1-carbonyl)amino]benzoate | 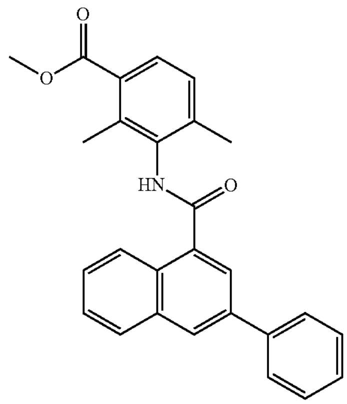 [SMILES: COC(=O)c1ccc(C)c(NC(=O)c2cc(-c3ccccc3)cc3ccccc23)c1C] | 410.2 (M + H)+ |
| 59 | Methyl 3-[[3-[3-(hydroxymethyl)phenyl]naphthalene-1-carbonyl]amino]-2,4-dimethyl-benzoate | 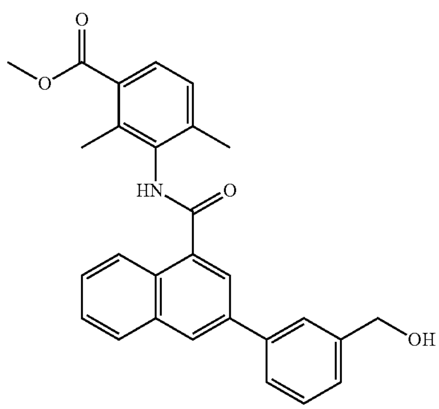 [SMILES: COC(=O)c1ccc(C)c(NC(=O)c2cc(-c3cccc(CO)c3)cc3ccccc23)c1C] | 440.2 (M + H)+ |
| 60 | Methyl 3-[[3-(3-chlorophenyl)naphthalene-1-carbonyl]amino]-2,4-dimethyl-benzoate | | 444.1 (M + H)+ | a) $^1$H NMR (400 MHz, DMSO): 10.23 (s, 1H), 8.37-8.36 (m, 1H), 8.32-8.30 (m, 1H), 8.12 (d, J = 1.9 Hz, 1H), 8.11-8.08 (m, 1H), 7.83-7.83 (m, 1H), 7.76-7.74 (m, 3H), 7.62-7.59 (m, 2H), 7.49 (t, J = 7.7 Hz, 1H), 7.38-7.36 (m, 1H), 5.29 (t, J = 5.7 Hz, 1H), 4.61-4.60 (m, 2H), 4.30 (q, J = 7.1 Hz, 2H), 2.39 (s, 6H), 1.31 (t, J = 7.1 Hz, 3H).

EXAMPLE 37

4-[[2-[3-(Hydroxymethyl)phenyl]quinoline-4-carbonyl]amino]-3,5-dimethyl-benzoic acid

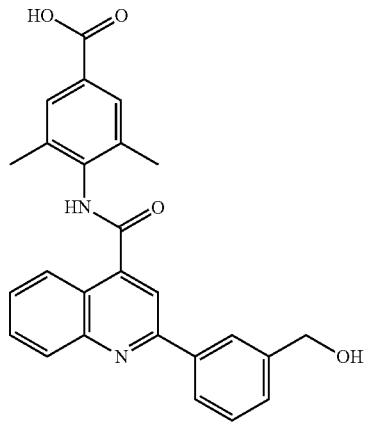 [SMILES: Cc1cc(C(=O)O)cc(C)c1NC(=O)c1cc(-c2cccc(CO)c2)nc2ccccc12]

Scheme 15, Step C.

A solution of aqueous 1N NaOH (1.9 ml) is added to a stirred solution of ethyl 4-[[2-[3-(hydroxymethyl)phenyl]quinoline-4-carbonyl]amino]-3,5-dimethyl-benzoate (0.42 g, 0.920 mmol) in THF (10.0 ml) and MeOH (3.0 ml). After heating at 40° C. for 12 hours, the reaction mixture is acidified to pH 1-2 with aqueous 1N HCl solution. The resulting precipitate is filtered, washed with water, and dried at 40° C. in vacuum oven for 1 hour to give the title compound as white solid (333.0 mg, 84.9%). Mass spectrum (m/z): 427.2 (M+H)$^+$.

The following compounds are prepared essentially by the method described above in Example 37, using the appropriate carboxylic ester:

| Example | Chemical Name | Structure | MS (m/z) |
|---|---|---|---|
| 38 | 3-[[2-[3-(Hydroxymethyl)phenyl]quinoline-4-carbonyl]amino]-2,4-dimethyl-benzoic acid | 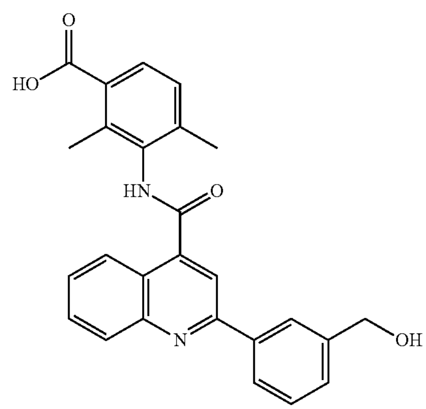 [SMILES: Cc1ccc(C(=O)O)c(C)c1NC(=O)c1cc(-c2cccc(CO)c2)nc2ccccc12] | 427.2 (M + H)$^+$ |
| 39 | 3,5-Dimethyl-4-[(3-phenylnaphthalene-1-carbonyl)amino]benzoic acid | 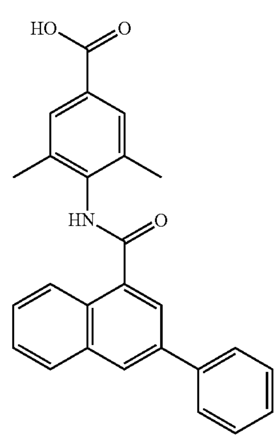 [SMILES: Cc1cc(C(=O)O)cc(C)c1NC(=O)c1cc(-c2ccccc2)cc2ccccc12] | 396.0 (M + H)$^+$ |

-continued

| Example | Chemical Name | Structure | MS (m/z) |
|---|---|---|---|
| 40 | 4-[[3-[3-(Hydroxymethyl)phenyl]naphthalene-1-carbonyl]amino]-3,5-dimethyl-benzoic acid | 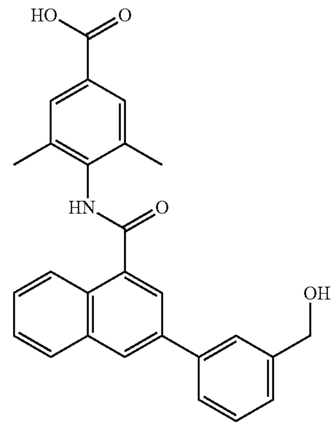 [SMILES: Cc1cc(C(=O)O)cc(C)c1NC(=O)c1cc(-c2cccc(CO)c2)cc2ccccc12] | 426.0 (M + H)⁺ |
| 41 | 2,4-Dimethyl-3-[(3-phenylnaphthalene-1-carbonyl)amino]benzoic acid | 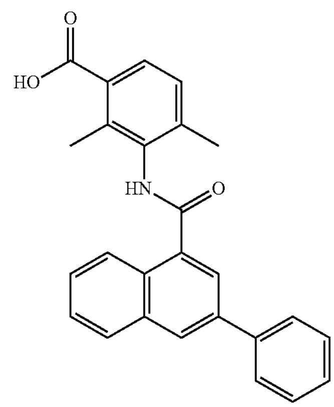 [SMILES: Cc1ccc(C(=O)O)c(C)c1NC(=O)c1cc(-c2ccccc2)cc2ccccc12] | 396.2 (M + H)⁺ |
| 42 | 3-[[3-[3-(Hydroxymethyl)phenyl]naphthalene-1-carbonyl]amino]-2,4-dimethyl-benzoic acid | 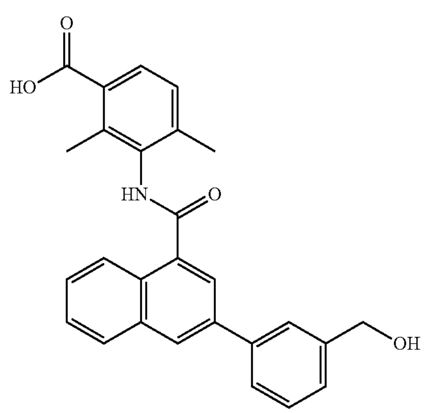 [SMILES: Cc1ccc(C(=O)O)c(C)c1NC(=O)c1cc(-c2cccc(CO)c2)cc2ccccc12] | 426.0 (M + H)⁺ |

| Example | Chemical Name | Structure | MS (m/z) |
|---|---|---|---|
| 43 | 3-[[3-[3-Chlorophenyl)naphthalene-1-carbonyl]amino]-2,4-dimethyl-benzoic acid | 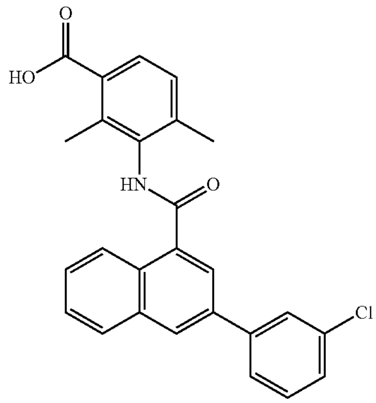 [SMILES: Cc1ccc(C(=O)O)c(C)c1NC(=O)c1cc(-c2cccc(Cl)c2)cc2ccccc12] | 430.1 (M + H)+ |

Preparation 61

Methyl 3-[(3-bromonaphthalene-1-carbonyl)amino]-2,4-dimethyl-benzoate

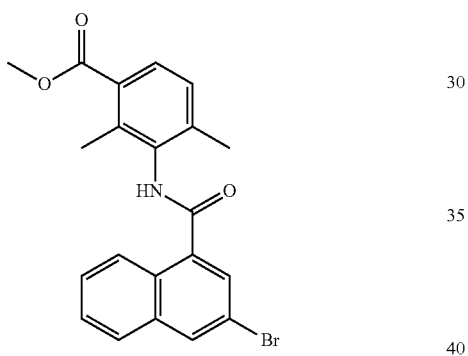

To a solution of 3-bromonaphthalene-1-carboxylic acid (0.42 g, 1.67 mmol) and methyl 3-amino-2,4-dimethylbenzoate (0.30 g, 1.67 mmol) in $CH_3CN$ (10.0 ml) at 0° C. is added phosphorus trichloride (0.292 ml, 3.35 mmol). After heating at 100° C. in a microwave reactor for 1.5 hours, the reaction mixture is diluted with water and extracted with EtOAc. The combined organic layers are dried over magnesium sulfate, filtered, and concentrated under reduced pressure to give the title compound as off white foam (0.60 g, 86.7%). Mass spectrum (m/z): 412.0 (M+H)+.

Scheme 16

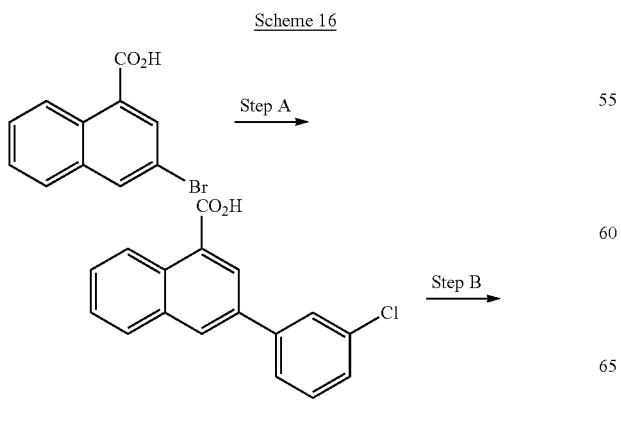

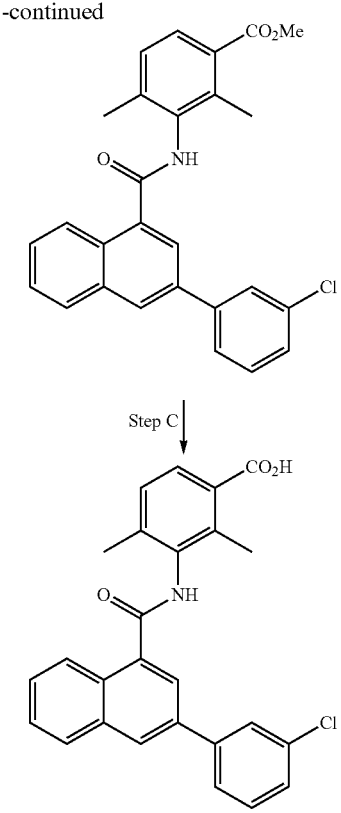

Alternate Preparation of 3-[[3-(3-Chlorophenyl)naphthalene-1-carbonyl]amino]-2,4-dimethyl-benzoic acid (Example 43)

Scheme 16, Step A.

Charge a reactor with 10 L of water and 585 g (6.970 mol) of sodium bicarbonate. Heat the solution to 50° C. and sparge with nitrogen for 15 min. Add 500 g (1.991 mol) of 3-bromo-1-naphthalene carboxylic acid and heat the mixture to 75° C. Add 4.47 g (19.9 mmol) of palladium acetate. Add 358 g (2.290 mol) of 3-chlorophenylboronic acid by portions of 50 g over 1 h. Stir for 2 h at 75° C. Cool to 25° C. and add 2 L of water, 0.5 L of 25% aqueous sodium hydroxide and 1.5 L of THF. Wash the aqueous solution with 2×2 L of heptanes. Add 10 L of THF and 2.5 L of ethyl acetate to the washed aqueous solution. Add 890 g of 37% HCl to bring the pH to approx 2. Separate the phases and extract the aqueous phase with a mixture of 2 L of THF and 0.5 L of ethyl acetate. Wash the combined organic solutions with 1 L of brine. Treat the solution with 100 g of activated carbon at 20° C. for 1 h and filter the mixture over diatomaceous earth. Add 400 g of metal scavenging silica and heat the suspension to 50° C., then stir at 50° C. for 4 h. Cool to 20° C. and remove the silica by filtration. Repeat the operation with another charge of 400 g part of scavenger. Cool to 20° C., remove the scavenger by filtration and evaporate the solution to dryness under reduced pressure. Dissolve the crude material in 8 L of THF and add 12 L of heptanes. Filter the solution over a pad of 900 g of silica and elute with 4×900 mL of a mixture of THF and heptanes 2-3. Evaporate the filtrate under reduced pressure to give a suspension. Collect the solids by filtration and dry at 50° C. under 2-10 mBar for 4 h to give 502 g (89%) of 3-(3-chlorophenyl)naphthalene-1-carboxylic acid. $^1$H NMR (400 MHz, DMSO) δ 7.48-7.51 (m, 1H), 7.56 (t, J=8.1 Hz, 1H), 7.61-7.69 (m, 2H), 7.81-7.83 (m, 1H), 7.92 (d, J=2.2 Hz, 1H), 8.10-8.13 (m, 1H), 8.42 (d, J=2.2 Hz, 1H), 8.54 (d, J=2.2 Hz, 1H), 8.85 (d, J=8.4 Hz, 1H), 13.35 (br s, 1H).

Scheme 16, Step B.

Charge a 20 L reactor with 485 g (1.715 mol) of 3-(3-chlorophenyl)naphthalene-1-carboxylic acid, 136 g of pyridine (1.715 mol) and 4.85 L of toluene. Heat the mixture to 75° C. and add 306 g (2.573 mol) of thionyl chloride over about 15 min Stir the reaction mixture for 3 h at 75° C. and add 102 g (0.858 mol) of thionyl chloride to consume remaining starting acid. After stirring the reaction mixture for 1 h, decant the upper layer and discard the lower waste layer at 75° C. Add 102 g (0.858 mol) of thionyl chloride and 34 g (0.429 mol) of pyridine. Stir the reaction mixture for 1 h at 75° C. Hold the reaction mixture overnight at 20-25° C. Wash the organic layer with 2×0.5 L of water. Add a solution of 370 g (1.715 mol) of methyl 3-amino-2,4-dimethyl-benzoate in 2.425 L of water to the reactor in one portion. Add a solution of 859 g (8.577 mol) of potassium bicarbonate in 4.850 L of water over 40 min. Stir the reaction mixture for 2 h at 20-25° C. Add 4.850 L of THF, and stir until all the solids dissolve. Decant and discard the lower aqueous phase. Wash the upper organic phase with a solution of 2.57 g of Na$_2$S-9H$_2$O in 0.970 L of water and discard the aqueous phase. Wash the organic layer three times with 0.970 L of brine, then with 0.970 L of 1N hydrochloric acid, and finally with 0.970 L of brine. Dry the organic phase over sodium sulfate. Concentrate the product solution (THF-Toluene) under reduced pressure to remove the THF. Seed the batch with crystalline product and allow the temperature to decrease from 45° C. to 37° C. over approx 1 h. As crystallization progresses, add 1.94 L of toluene and lower the temperature to 20° C. Collect the product by filtration after 2 h of stirring. Wash the product cake with 1.94 L of TBME and dry at 80° C. under 2-10 Torr to constant weight. Dissolve the solid in 0.970 L of acetone at 55° C. and add 1.940 L of TBME. Cool the solution to 20° C. over 1 h to crystallize the product. Collect the white crystalline solid by filtration after 2 h of stirring at 20° C. and dry at 80° C. under 2-10 Torr until constant weight. Purify the material by chromatography over a short pad of silica (1.5 kg, 3 parts) eluted with dichloromethane to give 442 g (58%) of methyl 3-[[3-(3-chlorophenyl)naphthalene-1-carbonyl]amino]-2,4-dimethyl-benzoate as a white solid. $^1$H NMR (400 MHz, DMSO) δ 2.41 (s, 3H), 2.53 (s, 3H), 3.85 (s, 3H), 7.30 (d, J=8.0 Hz, 1H), 7.51 (d, J=8.0 Hz, 1H), 7.59 (d, J=8.0 Hz, 1H), 7.63-7.65 (m, 2H), 7.69 (d, J=8.0 Hz, 1H), 7.90 (d, J=8.0 Hz, 1H), 8.02 (s, 1H), 8.10-8.14 (m, 1H), 8.20 (s, 1H), 8.37-8.40 (m, 1H), 8.46 (s, 1H), 10.20 (br s, 1H).

Scheme 16, Step C.

Charge a 20 L reactor with 178 g (3.176 mol) of potassium hydroxide and 1.59 L of water. Stir the mixture until complete dissolution. Add 4.70 L of isopropanol and heat the solution 65° C. Add a solution of 470 g (1.059 mol) of methyl 3-[[3-(3-chlorophenyl)naphthalene-1-carbonyl]amino]-2,4-dimethyl-benzoate in 1.88 L of THF to the reactor at 65° C. in about 1 h. After the end of the addition, stir the reaction mixture for 2 h at 65° C. Add 23.5 g of active carbon and stir the mixture at 65° C. for 1 h. Cool the mixture to 20° C. and filter over diatomaceous earth. Rinse the cake with 0.94 L of isopropanol followed by 2×0.94 L of water. Concentrate the solution under reduced pressure to remove the organic solvents. Transfer the aqueous solution to a 10 L reactor and dilute with 3.76 L of water. Acidify to pH 3.0 by adding 0.95 L of 3 N HCl. Add 0.94 L of isopropanol and stir the suspension overnight at 20° C. Collect the product by filtration and wash with 2.82 L of water. Dry the crude product at 50° C. over the weekend. Transfer the dried solid to a 20 L reactor, add 4.70 L of acetone and heat the suspension to reflux for 2 h. Cool the suspension to 20° C. over 3 h and hold at this temperature overnight. Cool the suspension to 8° C. and stir for 1 h. Collect the product by filtration and wash the cake with 1.41 L of acetone. Dry at 50° C. under 2-10 Torr overnight to give the title compound as a white solid (378.0 g, 83% yield). Mass spectrum (m/z): 430.3 (M+H)$^+$.

In Vitro Binding to Human EP1, EP2, EP3 and EP4 hEP1 and hEP4 membranes are prepared from recombinant HEK293 cells stably expressing human EP1 (Genbank accession number AY275470) or EP4 (Genbank accession number AY429109) receptors. hEP2 and hEP3 membranes are prepared from HEK293 cells transiently transfected with EP2 (Genbank accession number AY275471) or EP3 (isoform VI: Genbank accession number AY429108) receptor plasmids. Frozen cell pellets are homogenized in homogenization buffer using a Teflon/glass homogenizer. Membrane protein is aliquoted and quick frozen on dry ice prior to storage at −80° C. Homogenization buffer contained 10 mM Tris-HCl, pH 7.4, 250 mM sucrose, 1 mM EDTA, 0.3 mM indomethacin and plus Complete™, with EDTA, obtained from Roche Molecular Biochemicals (Catalog Number 1 697 498).

Kd values for [$^3$H]-PGE$_2$ binding to each receptor are determined by saturation binding studies or homologous competition. Compounds are tested in a 96-well format using a three-fold dilution series to generate a 10-point curve. Diluted compound is incubated with 20 μg/well EP1, 10 μg/well EP2, 1 μg/well EP3 or 10 to 20 μg/well EP4 membrane for 90 minutes at 25° C. in the presence of 0.3 to 0.5 nM [$^3$H]-PGE$_2$ (PerkinElmer, 118 to 180 Ci/mmol). The binding reaction is performed in 200 μL MES buffer (10 mM MES pH 6.0 with KOH, 10 mM MgCl$_2$ and 1 mM EDTA) using 0.5 mL polystyrene 96-well deep-well plates. Non-specific binding is calculated by comparing binding in the presence and absence of 2 μM of PGE$_2$. The membranes are harvested by filtration (TomTek harvester), washed 4 times with cold buffer (10 mM MES pH 6.0 with KOH, 10 mM MgCl$_2$), dried in a 60° C. oven, and the radioactivity is quantified as counts per minute (CPM) using a TopCount detector. Percent specific binding is calculated as the percent of the binding in the absence of any inhibitor, corrected for binding in the presence of 2 uM of $PGE_2$. Data are analyzed using a 4-parameter nonlinear logistic equation (ABase Equation 205) as shown: y=(A+((B−A)/(1+((C/x)^D)) where, y=% specific inhibition, A=bottom of the curve; B=top of the curve; C=relative $IC_{50}$=concentration causing 50% inhibition based on the range of the data from top to bottom; D=Hill, Slope=slope of the curve. $K_i$ conversion from $IC_{50}$ Values ($K_i=IC_{50}/(1+[L]/K_d)$ where [L] is the ligand concentration). Results are expressed as the geometric mean±standard deviation; n=number of independent determinations. The standard deviation is calculated by the delta method, being $SD_{log\ Ki}$×geometric mean×ln(10).

The compounds of Examples 1-43 herein are tested essentially as described above and exhibit a $K_i$ value for hEP4 of lower than 1 μM.

TABLE 1

In vitro binding of Example 1 to human EP1, EP2, EP3 and EP4

| Test Compound | hEP1, $K_i$ (nM) | hEP2, $K_i$ (nM) | hEP3, $K_i$ (nM) | hEP4, $K_i$ (nM) |
|---|---|---|---|---|
| Example 1 | >18800 (n = 1) | 5850 ± 1010 (n = 2) | >14800 (n = 1) | 2.18 ± 1.74 (n = 5) |
| Example 22 | >17500 (n = 1) | >18900 (n = 1) | >14000 (n = 1) | 2.07 ± 1.31 (n = 8) |

The data in Table 1 demonstrate the compounds of Example 1 and Example 22 bind to hEP4 more strongly than to hEP1, hEP2, and hEP3 indicating selectivity for the hEP4 receptor.

In Vitro Human EP4 Functional Antagonist Activity

Assays are conducted in recombinant HEK293 cells stably expressing human EP4 receptor. The cell lines are maintained by culturing in DMEM with high glucose and pyridoxine hydrochloride (Invitrogen) supplemented with 10% fetal bovine serum (FBS), 1 mM sodium pyruvate, 10 mM HEPES, 500 geneticin and 2 mM L-glutamine. Confluent cultures are grown at 37° C. in an atmosphere containing 5% $CO_2$. Cells are harvested using 2.5% Trypsin-EDTA, suspended in freeze media (FBS with 6% DMSO) at $10^7$ cells/mL and aliquots are stored in liquid nitrogen. Just before assay, cells are thawed in DMEM, centrifuged, and resuspended in cAMP buffer.

The inhibition of $PGE_2$-stimulated cAMP production by EP4 antagonists is measured using HTRF; (Cisbio catalog #62AM4PEB). An aliquot equivalent to 4000 cells is incubated with 50 μL cAMP assay buffer containing $EC_{80}$ of $PGE_2$ (0.188 nM $PGE_2$ from Sigma, catalog # P5640-10 mg) and antagonists at room temperature for 20 minutes. cAMP assay buffer contains 500 mL HBSS (Hank's Balanced Salt Solution), 0.1% BSA, 20 mM HEPES and 200 μM IBMX (Sigma 15879). CJ-042794 (4-{(1S)-1-[({5-chloro-2-[(4-fluorophenyl)oxy]phenyl}carbonyl)amino]ethyl}benzoic acid) serves as a positive control (See Murase, A., et al., *Life Sciences*, 82:226-232 (2008)). To measure the cAMP levels, cAMP-d2 conjugate and anti cAMP-cryptate conjugate in lysis buffer are incubated with the treated cells at room temperature for 1 hour. The HTRF signal is detected using an EnVision® plate reader (Perkin-Elmer) to calculate the ratio of fluorescence at 665 nm to 620 nm. The raw data are converted to cAMP amount (pmole/well) using a cAMP standard curve generated for each experiment. Data are analyzed using a 4-parameter nonlinear logistic equation (ABase Equation 205) as shown: y=(A+((B−A)/(1+((C/x)^D)))) where, y=% specific inhibition, A=Bottom of the curve, B=Top of the curve, C=Relative $IC_{50}$=concentration causing 50% inhibition based on the range of the data from top to bottom, D=Hill, Slope=slope of the curve. Results are expressed as the geometric mean±standard deviation; n=number of independent determinations. The standard deviation is calculated by the delta method, being $S_{log\ IC50}$×geometric mean×ln(10).

Following the procedures essentially as described above, the compound of Example 1 has an $IC_{50}$ of 2.31±2.02 nM (n=2) demonstrating that the compound of Example 1 is an antagonist of human EP4 in vitro.

In Vitro Rat EP4 Functional Antagonist Activity

Rat EP4 cDNA (Genebank Accession# NM 03276) is cloned into pcDNA 3.1 vector and subsequently transfected in HEK293 cells for receptor expression. Rat EP4 stable clone is scaled up and then frozen down as cell bank for future compounds screening. To test EP4 antagonist compounds in rEP4 cells, thaw the frozen cells and then resuspend cells in cAMP assay buffer. The cAMP buffer is made by HBSS without Phenol Red (Hyclone, SH30268) supplemented with 20 mM HEPES (Hyclone, SH30237), 0.1% BSA (Gibco, 15260) and 125 μM IBMX (Sigma, 15879). The cells are plated into 96-well half area flat-bottom polystyrene black plates (Costar 3694). Compounds are serial diluted with DMSO to give 10-point concentration response curves. Then diluted compounds are added into cAMP assay buffer which contains $PGE_2$ (Cayman 14010, in a concentration predetermined to produce an $EC_{80}$) at ratio of DMSO/buffer at 1/100. The cells are treated with compounds in the presence of $PGE_2$ ($EC_{80}$ concentration) for 30 minutes at room temperature. The cAMP levels generated from the cells are quantified by a cAMP HTRF assay kit (Cisbio 62AM4PEC). The plates are read on an EnVision plate reader using HTRF optimized protocol (PerkinElmer). $IC_{50}$'s are calculated using Graphpad Prism (v. 4) nonlinear regression, sigmoidal dose response curve fitting.

Following the procedures essentially as described above, the compound of Example 1 has an $IC_{50}$ of 1.51 nM measured at rat EP4. This demonstrates that the compound of Example 1 is an antagonist of rat EP4 in vitro.

In Vitro Antagonist Activity in Human Whole Blood

The inhibitory effects of $PGE_2$ on LPS-induced TNFα production from macrophages/monocytes are believed to be mediated by EP4 receptors (See Murase, A., et al., *Life Sciences*, 82:226-232 (2008)). The ability of the compound of Example 1 to reverse the inhibitory effect of $PGE_2$ on LPS-induced TNFα production in human whole blood is an indicia of functional activity.

Blood is collected from normal volunteer donors into sodium heparin vacutainer tubes. Donors have not taken NSAIDs or celecoxib within 48 hours or glucocorticoids within two weeks of the donation. All tubes/donor are pooled into 50 mL Falcon conical centrifuge tubes and 98 μL/well is distributed into 96-well tissue culture plates (Falcon 3072). Compounds are diluted into DMSO to 100× final and 1 μL/well in triplicate is added to the blood to give 7 point concentration response curves. The blood is pretreated with the compounds at 37° C., in a 5% $CO_2$ humidified atmosphere, for 30 minutes, after which 1 μL/well of a solution of 1 mg/mL of lipopolysaccharide (LPS) (Sigma 0111:B4) in 0.2 mg/mL bovine serum albumin (BSA)/PBS+/−1 mM $PGE_2$ (Cayman 14010) is added to give a final LPS concentration of 10 μg/mL+/−10 nM $PGE_2$. The plates are incubated for 20-24 hours at 37° C. in a 5% $CO_2$ humidified atmosphere. The plates are centrifuged at 1800× g, 10 minutes at 22° C., in an Eppendorf 5810R centrifuge. Plasma is removed from the cell layer and is transferred to v-bottom polypropylene plates. TNFα levels in 2 μL plasma are quantified by a commercially available enzyme immunoassay (R&D Systems DY210), using Immulon 4 HBX plates (Thermo 3855) and 3,3',5,5' tetramethylbiphenyl-4,4'-diamine substrate (KPL 50-76-03). The plates are read at $A_{450}$-$A_{650}$ on a plate reader (Molecular Devices Versamax) using SOFTmaxPRO (v. 4.3.1) software. $IC_{50}$s are calculated using Graphpad Prism (v. 4) nonlinear regression, sigmoidal dose response curve fitting. Results are expressed as the geometric mean±standard deviation; n=number of independent determinations. The standard deviation is calculated by the delta method, being $SD_{log\ IC50}$×geometric mean×ln(10).

Following the procedures essentially as described above, the compound of Example 1 has an $IC_{50}$ of 0.0595±0.0378 μM (n=3). This demonstrates that the compound of Example 1 is an EP4 antagonist in the human blood TNFα induction assay.

We claim:

1. A compound selected from a group consisting of
   3-[[6-(1,3-benzodioxol-5-yl)-3-methyl-pyridine-2-carbonyl]amino]-2,4-dimethyl-benzoic acid;
   3-[[6-[3-(hydroxymethyl)phenyl]-3-methyl-pyridine-2-carbonyl]amino]-2,4-dimethyl-benzoic acid; and
   3-[[3-(3-chlorophenyl)naphthalene-1-carbonyl]amino]-2,4-dimethyl-benzoic acid, or a pharmaceutically acceptable salt thereof.

2. The compound or salt according to claim 1 which is 3-[[6-(1,3-benzodioxol-5-yl)-3-methyl-pyridine-2-carbonyl]amino]-2,4-dimethyl-benzoic acid.

3. The compound or salt according to claim 1 which is 3-[[6-[3-(hydroxymethyl)phenyl]-3-methyl-pyridine-2-carbonyl]amino]-2,4-dimethyl-benzoic acid.

4. The compound or salt according to claim 1 which is 3-[[3-(3-chlorophenyl)naphthalene-1-carbonyl]amino]-2,4-dimethyl-benzoic acid.

5. A pharmaceutical composition, comprising a compound or a pharmaceutically acceptable salt thereof according to claim 2 with one or more pharmaceutically acceptable carriers, diluents, or excipients.

6. A pharmaceutical composition, comprising a compound or a pharmaceutically acceptable salt thereof according to claim 3 with one or more pharmaceutically acceptable carriers, diluents, or excipients.

7. A pharmaceutical composition, comprising a compound or a pharmaceutically acceptable salt thereof according to claim 4 with one or more pharmaceutically acceptable carriers, diluents, or excipients.

* * * * *

UNITED STATES PATENT AND TRADEMARK OFFICE
CERTIFICATE OF CORRECTION

PATENT NO.        : 10,005,721 B2
APPLICATION NO.   : 15/030891
DATED             : June 26, 2018
INVENTOR(S)       : Maria Jesus Blanco-Pillado et al.

Page 1 of 1

It is certified that error appears in the above-identified patent and that said Letters Patent is hereby corrected as shown below:

On the Title Page

Column 1 (Notice), Line 3, after "0 days." delete "days.".

Signed and Sealed this
Twenty-eighth Day of August, 2018

Andrei Iancu
*Director of the United States Patent and Trademark Office*